United States Patent
Omori et al.

(10) Patent No.: US 8,157,793 B2
(45) Date of Patent: Apr. 17, 2012

(54) MANIPULATOR FOR MEDICAL USE

(75) Inventors: Shigeru Omori, Ashigarakami-gun (JP);
Shuichi Uenohara, Fujinomiya (JP);
Makoto Jinno, Ota-ku (JP); Takamitsu Sunaoshi, Yokohama (JP)

(73) Assignees: Terumo Kabushiki Kaisha, Tokyo (JP);
Kabushiki Kaisha Toshiba, Tokyo (JP)

( * ) Notice: Subject to any disclaimer, the term of this patent is extended or adjusted under 35 U.S.C. 154(b) by 1216 days.

(21) Appl. No.: 11/874,522

(22) Filed: Oct. 18, 2007

(65) Prior Publication Data
US 2008/0103491 A1    May 1, 2008

Related U.S. Application Data

(60) Provisional application No. 60/862,820, filed on Oct. 25, 2006.

(30) Foreign Application Priority Data

Aug. 8, 2007    (JP) .................................. 2007-206849

(51) Int. Cl.
*A61B 17/00*    (2006.01)
(52) U.S. Cl. ........................................... 606/1; 606/130
(58) Field of Classification Search ............... 606/1, 130
See application file for complete search history.

(56) References Cited

U.S. PATENT DOCUMENTS

| 6,270,087 | B1 * | 8/2001 | Mickel et al. .................. 279/75 |
| 7,261,726 | B2 | 8/2007 | Jinno et al. |
| 2002/0072736 | A1 | 6/2002 | Tierney et al. |
| 2002/0087048 | A1 | 7/2002 | Brock et al. |
| 2004/0049205 | A1 | 3/2004 | Lee et al. |
| 2004/0092912 | A1 | 5/2004 | Jinno et al. |
| 2004/0133189 | A1 | 7/2004 | Sakurai |
| 2006/0161138 | A1 | 7/2006 | Orban, III et al. |

FOREIGN PATENT DOCUMENTS

| JP | 2004-105451 | 4/2004 |
| JP | 2004-208922 | 7/2004 |

* cited by examiner

*Primary Examiner* — Henry M Johnson, III
(74) *Attorney, Agent, or Firm* — Oblon, Spivak, McClelland, Maier & Neustadt, L.L.P.

(57) ABSTRACT

In a manipulator, an actuator block contains motors and rotary shafts extending from the motors. A working unit of the manipulator contains a connecting portion, attachable to and detachable from the actuator block. The connecting portion has pulleys connectable to ends of the rotary shafts, and has a locking plate movable by alignment pins. The locking plate has slits, which are engaged with plate-shaped portions formed on the upper ends of the pulleys. A coil spring is placed between the locking plate and a top plate.

6 Claims, 21 Drawing Sheets

MANIPULATOR FOR MEDICAL USE

BACKGROUND OF THE INVENTION

1. Field of the Invention

The present invention relates to a manipulator for medical use having an actuator unit and a working unit removable therefrom.

2. Description of the Related Art

According to laparoscopic surgery, it is customary to form a plurality of holes in the abdominal part of the patient, insert an endoscope and a forceps (or a manipulator) into the respective holes, and perform the surgical operation while images captured by the endoscope are being observed on a display monitor by the surgeon. Since such a laparoscopic surgical operation does not require the abdominal cavity to be opened, the burden on the patient is small and the number of days which the patient needs to recover and spend in the hospital until they are allowed to come out of hospital is greatly reduced. For these reasons, the laparoscopic surgical operation is expected to find an increased range of applications.

A manipulator system is composed of a manipulator body and a controller therefor, as described in Japanese Laid-Open Patent Publication No. 2004-105451, for example. The manipulator body contains an operating unit controlled by human and a working unit interchangeably removable from the operating unit.

The working unit (or an instrument) has a slender connecting shaft and an end working portion (also referred to as an end effector) disposed at the distal end of the connecting shaft. An actuator (a motor) for driving the end working portion via a wire is disposed in the operating unit. The wire is wound around a pulley in the vicinity of the proximal end. The motor in the operating unit is driven by the controller, whereby the wire is moved via the pulley.

The working unit does not contain an electron device such as a sensor in view of easily carrying out washing and sterilization. The positions or original points of the end working portion and the proximal end pulley cannot be directly detected, and the axial position of the end working portion is calculated based on rotation of the motor.

The working unit may be a gripper, a pair of scissors, an electric surgical knife, an ultrasonic surgical knife, a medical drill, or the like, and may be selected depending on a procedure in a laparoscopic operation. The working unit is removable from the operating unit, and when the working unit is attached to the operating unit, the pulley at the proximal end is engaged with a rotary shaft of the motor in the operating unit.

In such a system intended to connect a plurality of different working units to one operating unit, it is necessary to determine a motor phase as only one axial position, at which all the working units can be attached and detached (see Japanese Laid-Open Patent Publication No. 2004-105451, for example). The position is referred to as the original point (or the initial position).

Conventional manipulator systems are described in Japanese Laid-Open Patent Publication Nos. 2004-105451 and 2004-208922, etc.

In a system proposed in Japanese Laid-Open Patent Publication No. 2004-105451, it is unnecessary to take into consideration the motor excitation switching and electrical structure when the working unit is attached or detached.

In a system described in Japanese Laid-Open Patent Publication No. 2004-208922, a plurality of end tools (working units) are electrically attached and detached.

When surgery is traditionally performed, there is a long incision made so the surgeon can view and repair the internal parts of the patient. The long incision site can be a significant concern because it is subject to infection and is often the most traumatic and painful part of the patient's recover. In recent years, many surgeons have been using endoscopic tools and performing minimally invasive surgery, thereby vastly reducing the size of the incision.

Robotic tools have been developed to further improve the minimally invasive surgical process. These tools are highly specialized. They must perform the function that a surgeon would in a miniaturized manner. Surgeons perform many different functions on internal organs such as cutting, scraping, and suturing. Different surgical instruments are required for each of these functions. A different surgical device could be made for each surgical instrument, but it is most cost effective to simply change the surgical instrument mounted to the surgical instrument control unit for each function. To effectively implement interchangeability, each mounted surgical instrument must be safely and securely fastened to the surgical instrument control unit. Thus, there is a need for a device and a method for easily and reliably engaging surgical instruments with minimally invasive robotic surgical instrument control units. Further, there is a need for a mounting process that includes both engaging and locking steps such that surgical instruments can be used in a safe and efficient manner.

Further, the axial position of the end working portion is calculated based on, e.g. the original point of the motor. Thus, when a working unit is changed with another working unit during an operation, the other working unit needs to be precisely positioned at the original point. In other words, it is desirable that, when the working unit is detached from the operating unit, the working unit and the pulley are fixed at axial positions corresponding to the original point.

SUMMARY OF THE INVENTION

It is one of the objects of the present invention is to provide a manipulator for medical use, capable of automatically locking a working unit and a pulley at axial positions corresponding to the original points when the working unit is detached from an actuator unit.

It is one of the objects of the present invention is to automatically lock the working unit and a rotator at the axial positions corresponding to the original points such that a locking member is engaged with an engaging portion to prevent the rotation of the rotator when the working unit is separated from the actuator unit.

It is one of the objects of the present invention is to automatically lock the working unit and the rotator at the axial positions corresponding to the original points such that a noncircular portion is engaged with an engaging hole to prevent the rotation of the rotator by a locking plate when the working unit is separated from the actuator unit.

It is one of the objects of the present invention is to automatically lock the working unit and the rotator at the axial positions corresponding to the original points such that a locking plate is placed at a first position and a locking protrusion is engaged with a notch to prevent the rotation of the rotator when the working unit is separated from the actuator unit.

According to one aspect of the present invention, there is provided a manipulator for medical use, comprising an actuator unit containing a motor, and a working unit attachable to and detachable from the actuator unit, containing a connecting portion having a rotator connectable to a rotary shaft of the motor and a working portion coupled with the rotator. The connecting portion has a locking member, which is moved by a part of the actuator unit when the working unit is attached to or detached from the actuator unit. The locking member is engaged with an engaging portion of the rotator when the working unit is separated from the actuator unit, thereby preventing the rotator from rotating, and the locking member is separated from the engaging portion when the working unit is connected to the actuator unit, thereby making the rotator rotatable.

In the aspects of the present invention, the locking member is moved by a part of the actuator unit, and engaged with and separated from the engaging portion of the rotator. Thus, when the working unit is separated from the actuator unit, the locking member is engaged with the engaging portion to prevent the rotation of the rotator, and the working unit and the rotator are automatically locked at axial positions corresponding to the original points.

Further, according to another aspect of the present invention, the connecting portion may have a locking plate. The locking plate is moved by a part of the actuator unit when the connecting portion is attached to or detached from the actuator unit. The locking plate has an engaging hole, with which a noncircular portion of the rotator is engaged. The noncircular portion is engaged with the engaging hole when the working unit is separated from the actuator unit, thereby preventing the rotator from rotating, and the noncircular portion is separated from the engaging hole when the working unit is connected to the actuator unit, thereby making the rotator rotatable.

Thus, when the working unit is separated from the actuator unit, the noncircular portion is engaged with the engaging hole of the locking plate to prevent the rotation of the rotator, so that the working unit and the pulley are automatically locked at the axial positions corresponding to the original points.

In the aspects of the present invention, the term "the locking member is moved by a part of the actuator unit" means that the locking member is moved directly by the part or indirectly via another member.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Manipulators for medical use according to preferred embodiments of the present invention shall be described below with reference to FIGS. 1 through 21.

An end working portion 12 mounted on the distal end of the manipulator 10 according to a first embodiment serves to grip a portion of a living tissue, a curved needle, or the like for performing a certain operation, and is usually referred to as gripping forceps or a needle driver (needle holder).

Figure 1:
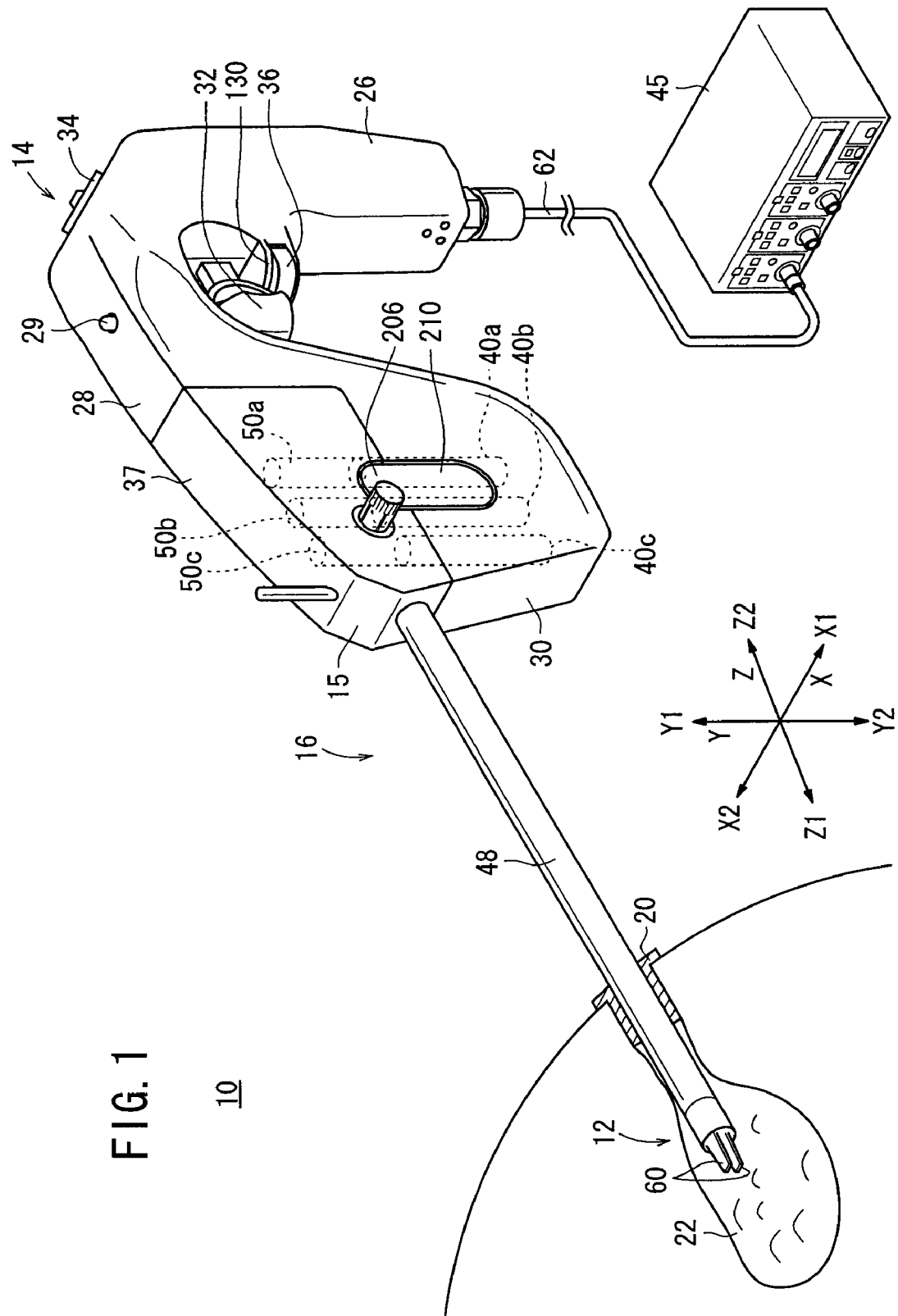
FIG. 1 is a perspective view of a manipulator according to a first embodiment of the present invention.
Figure 2:
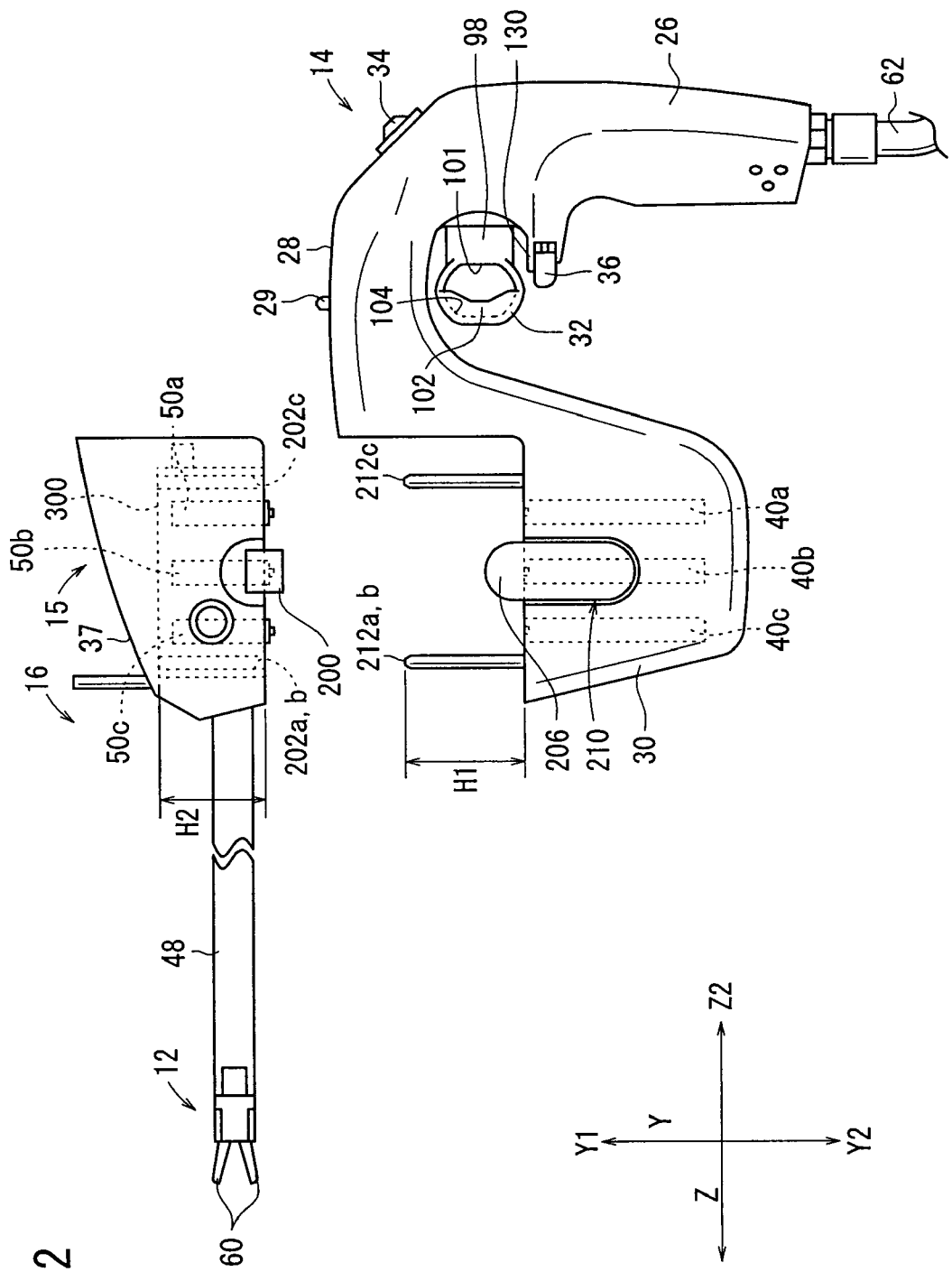
FIG. 2 is a side view of the manipulator, a working unit being separated from an operation command unit.

As shown in FIGS. 1 and 2, the manipulator 10 comprises an operation command unit 14 on a proximal end thereof which is held and operated by hand and a working unit 16 attachable to and detachable from the operation command unit 14.

It is assumed in the description which follows that the transverse direction of the manipulator 10 is referred to as X direction, vertical direction thereof as Y direction, and longitudinal directions of a connecting shaft 48 as Z direction in FIG. 1. Of the X directions, the rightward direction is referred to as an X1 direction, and the leftward direction as an X2 direction. Of the Y directions, the upward direction is referred to as a Y1 direction, and the downward direction as a Y2 direction. Of the Z directions, the forward direction is referred to as a Z1 direction, and the rearward direction as a Z2 direction. Unless otherwise noted, these directions represent directions of the manipulator 10 when it is of a neutral posture. The definition of the above directions is for illustrative purpose only, and the manipulator 10 can be used in any orientations, e.g., it may be used upside down.

The working unit 16 contains the end working portion 12 for carrying out a work, a connecting portion 15 that is connected to an actuator block (actuator unit) 30 of the operation command unit 14, and the long, hollow connecting shaft 48 for connecting the end working portion 12 and the connecting portion 15. The working unit 16 can be detached from the operation command unit 14 by operating the actuator block 30, and thus can be subjected to washing, sterilization, maintenance, etc.

The end working portion 12 and the connecting shaft 48 are thin, and thereby can be inserted through a cylindrical trocar 20 formed on an abdominal part of a patient, etc. into a body cavity 22. By controlling the operation command unit 14, various procedures such as diseased part resection, grasp, suture, and tie-knot can be carried out in the body cavity 22.

The operation command unit 14 contains a grip handle 26 that is grasped by a human hand, a bridge 28 extending from the upper portion of the grip handle 26, and the actuator block 30 connected to one end of the bridge 28.

As shown in FIG. 2, the grip handle 26 of the operation command unit 14 extends from the other end of the bridge 28 in the Y2 direction. The grip handle 26 has a length suitable for being grasped by a human hand, and has an input means of a trigger lever 32, a composite input part 34, and a switch 36. An LED 29 is disposed in a visible position on the upper surface of the bridge 28. The upper surface of the bridge 28 is easily visible even during a procedure, and suitable for disposing the LED 29.

A cable 62 connected to a controller 45 is disposed on the lower end of the grip handle 26. The grip handle 26 and the cable 62 may be connected by a connector.

In the operation command unit 14, the structure and function of the composite input part 34 will be described below.

The composite input part 34 is a composite input means for transmitting a command of rotating the end working portion 12 in the roll direction (the axial rotation direction) or the yaw direction (the horizontal direction). The trigger lever 32 is an input means for transmitting a command of opening and closing a gripper 60 (see FIG. 2) in the end working portion 12. The switch 36 is an input means for start-and-stop controlling the manipulator 10. The LED 29 is an indicator for showing the state of the manipulator 10, and has such a size that an operator can easily recognize the indication and such a light weight that the handling of the manipulator 10 is not affected. The LED 29 is disposed in an easily-visible position substantially at the center of the upper surface of the bridge 28.

Figure 3:
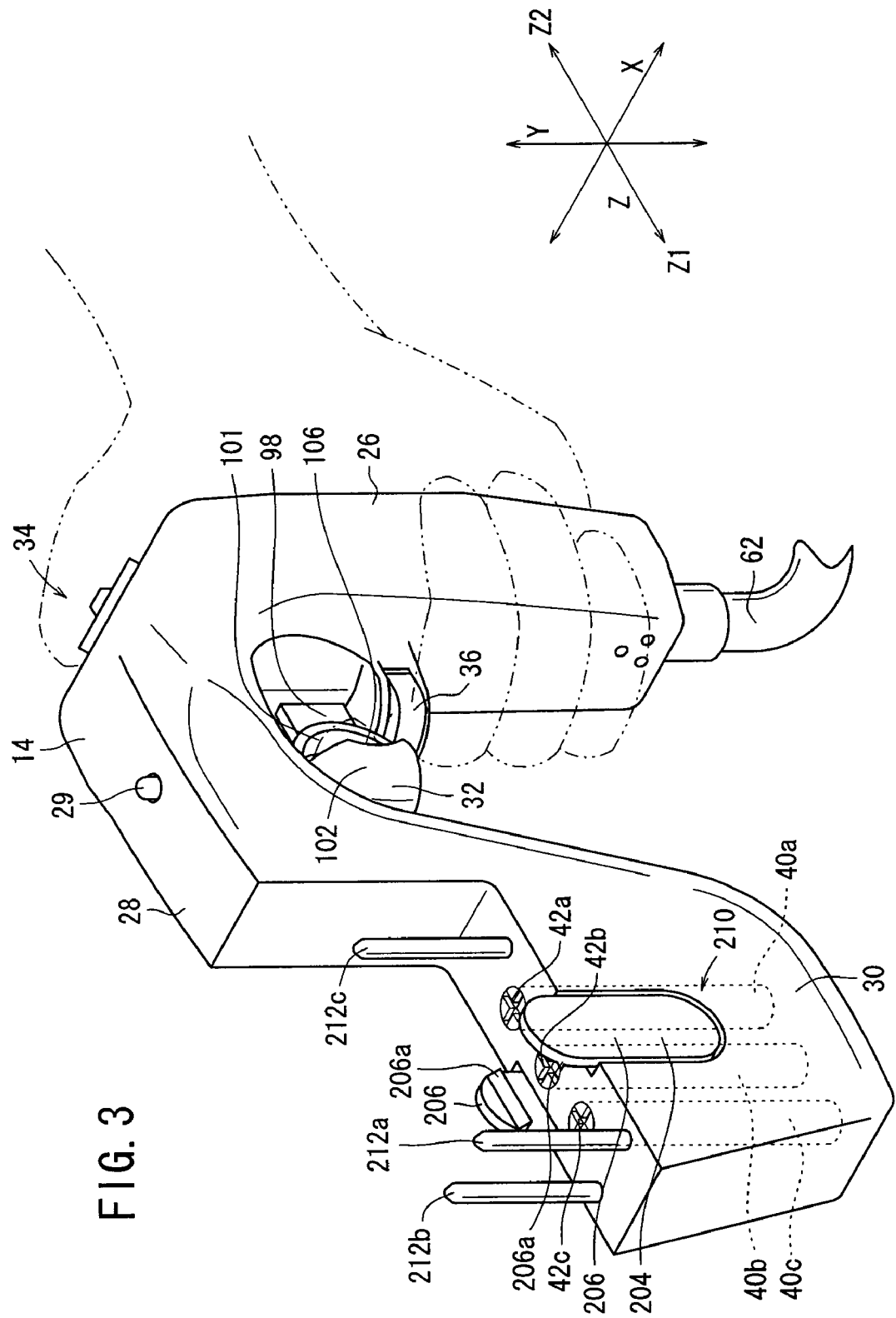
FIG. 3 is a perspective view of the operation command unit.

As shown in FIG. 3, the trigger lever 32 projects in the Z1 direction on the lower side of the bridge 28. The position of the trigger lever 32 is such that it can be easily handled by an index finger.

The trigger lever 32 is connected via an arm 98 to the grip handle 26, and can be moved close to and away from the grip handle 26. The arm 98 is connected to a sensor (not shown) in the grip handle 26, and the movement amount of the trigger lever 32 is measured by the sensor, so that the measurement is transmitted to the controller 45.

As shown in FIG. 3, the trigger lever 32 has a pull part 101 for pulling the trigger lever 32 by finger toward the grip handle 26 in the Z2 direction, and a push part 102 for pressing the trigger lever 32 by finger in the Z1 direction, the push part 102 facing the pull part 101.

In the operation command unit 14, a recess 104 is formed in the push part 102 of the trigger lever 32 to carry out a delicate operation while inserting a fingertip in the recess 104. Thus, the gripper 60, scissors, etc. in the end working portion 12 can be precisely opened and closed.

As shown in FIGS. 2 and 3, the switch 36 is an operation mechanism movable close to and away from the grip handle 26, and the trigger lever 32 and the switch 36 are arranged on the Z1 side of the grip handle 26 in the longitudinal direction of the grip handle 26 (the Y direction). The switch 36 is disposed immediately below the trigger lever 32 (on the Y2 side), and a thin plate 130 is placed between the switch 36 and the trigger lever 32.

The switch 36 is alternate, and by pushing an operation button 36a in the Z2 direction, the switch 36 is locked in the ON state. When the hand is released from the switch 36, the switch 36 is moved slightly toward the distal end and kept in the position. By pushing the switch 36 again, the switch 36 is switched from the ON state to the OFF state, and is moved toward the distal end in the Z1 direction by an elastic body (not shown), thereby returning to the initial position. The switch 36 can be kept in the ON or OFF state by these procedures, and it is not necessary to continue pushing the switch 36. Thus, the switch 36 only needs to be handled when the ON or OFF state is switched, and the trigger lever 32 can be handled at any time except when the ON/OFF state is switched. The switch 36 and the trigger lever 32 can be preferably used in combination in this manner.

The switch 36 acts to start up the system, and to return motors 40a through 40c to the original points, thereby stopping the system. The system is active when the switch 36 is in the ON state, and the system is stopped when in the OFF state. The active and stopped states of the system are indicated by lighting of the LED 29.

Then, the attachment and detachment between the connecting portion 15 of the working unit 16 and the operation command unit 14 will be described below.

As shown in FIG. 1, the connecting portion 15 is covered with a resin cover 37, and driven pulleys 50a, 50b, 50c are rotatably disposed in the connecting portion 15. A wire (not shown) is wound around each of the pulleys 50a, 50b, 50c, and extends through the hollow connecting shaft 48 to the end working portion 12.

Figure 4:
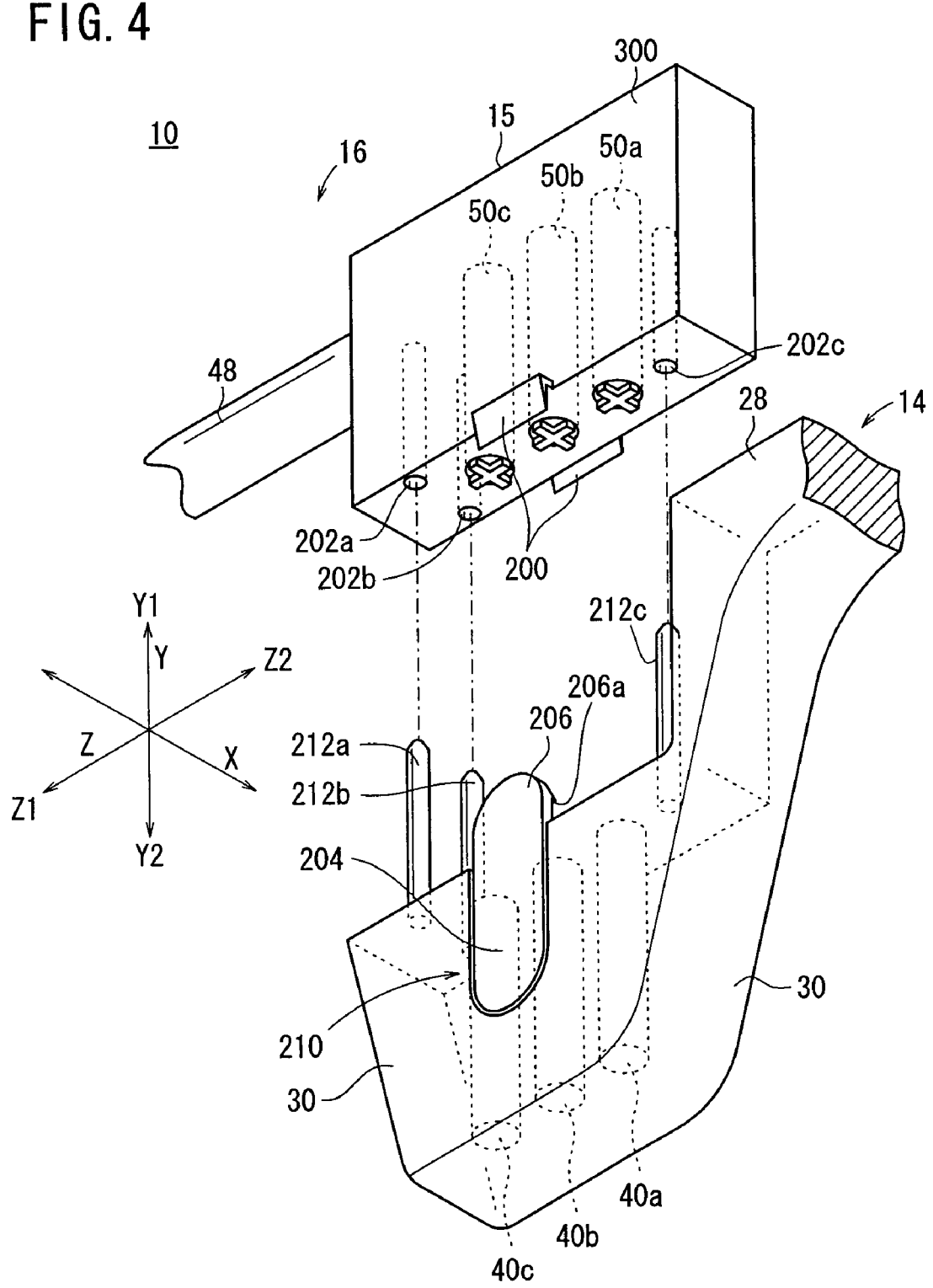
FIG. 4 is a perspective view obliquely from below of an actuator block of the operation command unit and a connecting portion of the working unit separated therefrom.

As shown in FIGS. 2 and 4, the connecting portion 15 has engaging pieces 200 on both sides thereof and has three downward mating holes 202a, 202b, 202c. The mating holes 202a to 202c are formed in the vicinity of the Z1 and Z2 direction ends, and extends in the Y1 direction.

In the actuator block 30, the motors 40a, 40b, 40c corresponding to the three-degree-of-freedom mechanism of the end working portion 12 are arranged in the longitudinal direction of the connecting portion 15. The pulleys 50a, 50b, 50c each have a cross-shaped connecting projection at the lower end in the Y2 direction, and rotary shafts 42a, 42b, 42c of the motors 40a to 40c each have a cross-shaped connecting recess. The connecting projections and the connecting recesses are engageable with each other, and thereby the rotary motions of the motors 40a to 40c are reliably transmitted to the pulleys 50a, 50b, 50c. The shapes of these engaging portions are not limited to the cross shape.

The motors 40a to 40c are small and thin, and the actuator block 30 has a compact flat shape. The actuator block 30 is disposed at the Z1 direction end of the operation command unit 14. The motors 40a to 40c are rotated by the operation command unit 14 or the trigger lever 32 under the control of the controller 45.

The actuator block 30 further has two separate engaging portions 210 for holding the connecting portion 15 of the working unit 16, and three alignment pins (components of the actuator unit) 212a, 212b, 212c for positioning and fixing the connecting portion 15. In FIGS. 4, 8, 9, and 11, the cover 37 (see FIG. 1) is not shown in order to easily understand the structure of the connecting portion 15.

The two engaging portions 210 are symmetrically disposed on both sides of the actuator block 30, and each have an operation surface 204 and a lever 206 extending in the Y1 direction from the operation surface 204. The levers 206 project from the upper surface of the actuator block 30 in the Y1 direction, and their ends are tapered. The engaging portions 210 are elastically urged under an elastic body (not shown), in such directions that the levers 206 are directed inward.

The alignment pins 212a to 212c extend in the Y1 direction on the upper surface of the actuator block 30 at positions facing the mating holes 202a to 202c, and two thereof are in the vicinity of the Z1 direction end and the other is in the vicinity of the Z2 direction end. The two alignment pins 212a, 212b are arranged in the X direction in the vicinity of the Z1 direction end.

The actuator block 30 has the three alignment pins 212a to 212c in this manner, whereby the connecting portion 15 is fixed at three points and can be easily reliably positioned. Further, the three alignment pins 212a to 212c are not arranged linearly, so that the connecting portion 15 can be stably fixed even when a twisting force is applied in any direction. The connecting portion 15 can be reliably positioned and stably fixed as long as the actuator block 30 has at least two of the alignment pins 212a to 212c. The connecting portion 15 can be stably fixed particularly by two alignment pins distant in the Z direction.

As shown in FIG. 2, the heights H1 of the alignment pins 212a to 212c are more than the height H2 of a pulley container 300 in the connecting portion 15 having the mating holes 202a to 202c. The alignment pins 212a to 212c suitably pierce through the pulley container 300.

The structure of the connecting portion 15 will be described in detail below with reference to FIGS. 5 to 9.

Figure 5:
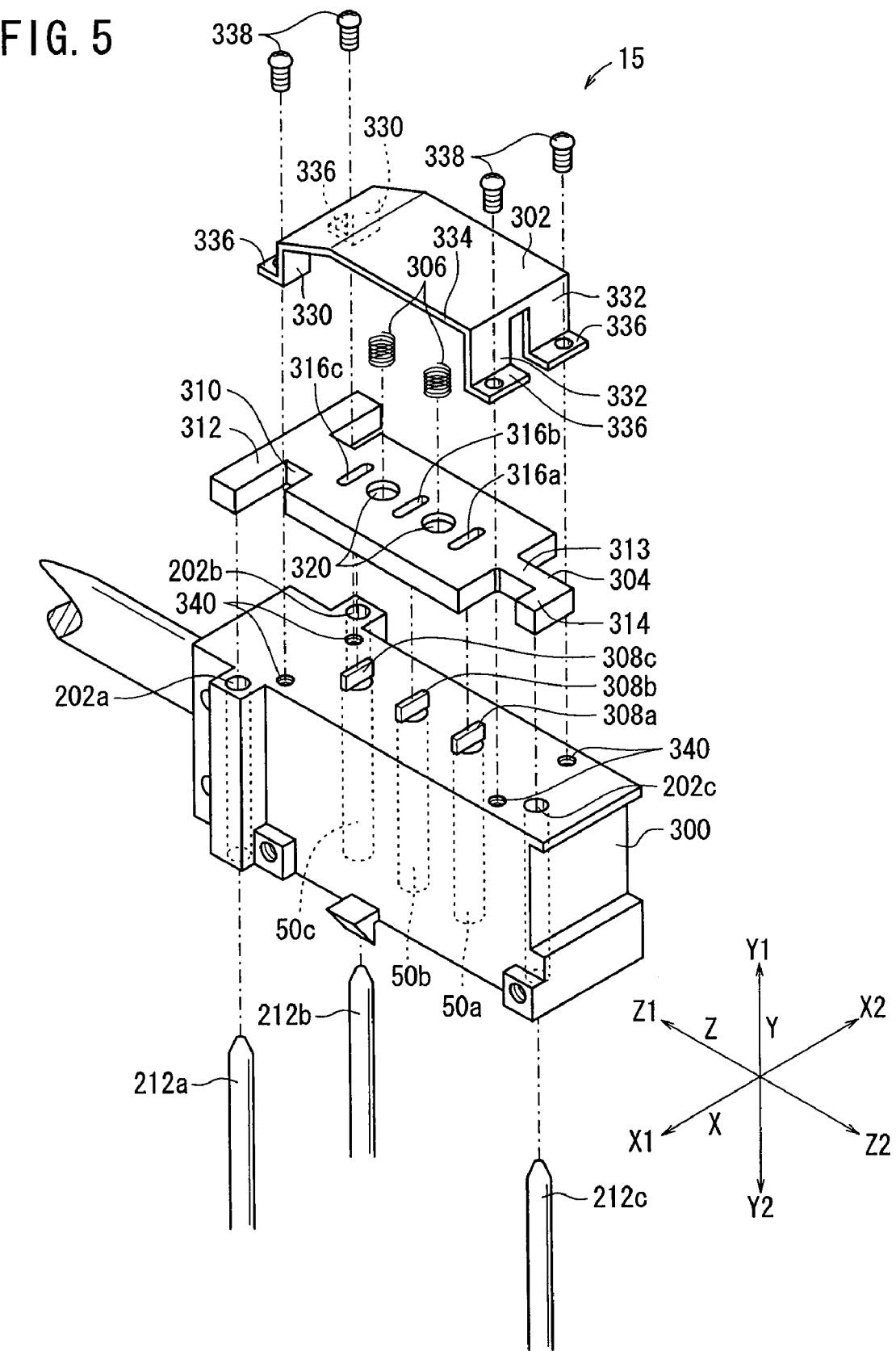
FIG. 5 is an exploded perspective view of the connecting portion.
Figure 6:
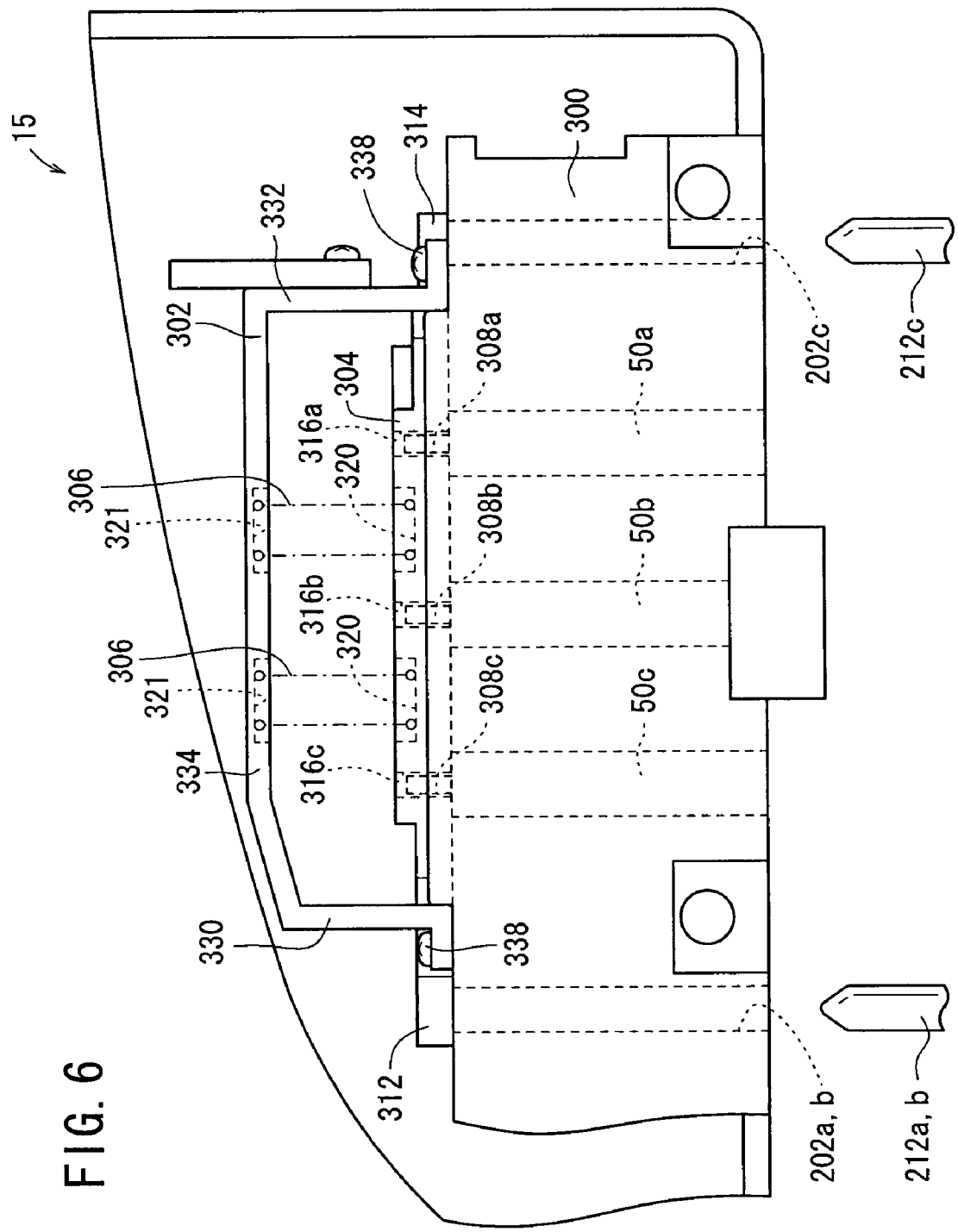
FIG. 6 is a side view of the connecting portion.

As shown in FIGS. 5 and 6, the connecting portion 15 has the pulley container 300 containing the pulleys 50a to 50c, an upper part 302 disposed on the pulley container 300, a locking plate 304, and two coil springs (elastic bodies) 306.

The pulleys 50a to 50c are arranged in the Z direction in the pulley container 300 as described above, and their upper ends project slightly from the upper surface of the pulley container 300 and have plate-shaped portions (engaging portions) 308a, 308b, 308c. The plate-shaped portions 308a to 308c have the same shape. Also, the plate-shaped portions 308a to 308c are disposed at positions corresponding to the diameters of the upper ends of the pulleys 50a to 50c, and slightly extend in the Y1 direction. When the pulleys 50a to 50c are at the original points, the plate-shaped portions 308a to 308c are directed in the X direction as viewed in plan.

The locking plate 304 is long in the Z direction, and has a wide part at the center. In the locking plate 304, a narrow part 310 and a T-shaped first end 312 are disposed in the Z1 direction, and a narrow part 313 and a second end 314 bent to the X1 direction are disposed in the Z2 direction. When the working unit 16 is attached to the operation command unit 14, the locking plate 304 is pushed up relatively in the Y1 direction such that the right and left of the lower surface of the first end 312 are in contact with the alignment pins 212a, 212b, and the lower surface of the second end 314 is in contact with the alignment pin 212c.

At the center of the locking plate 304, three slits (engaging holes) 316a, 316b, 316c, extending in the X direction, are arranged in the Z direction in the positions corresponding to the pulleys 50a, 50b, 50c. The Z direction widths of the slits 316a to 316c are slightly larger than the thicknesses of the plate-shaped portions 308a to 308c, and the X direction length of the slits 316a to 316c are slightly larger than those of the plate-shaped portions 308a to 308c, respectively.

On the upper surface of the locking plate 304, shallow circular recesses 320 are formed between the slits 316a and 316b and between the slits 316b and 316c. The diameters of the circular recesses 320 are slightly larger than those of the coil springs 306, and the lower ends of the coil springs 306 are attached therein. Two circular recesses 321 (see FIG. 6) equal to the circular recesses 320 are formed on the lower surface of the upper part 302, and the upper ends of the coil springs 306 are attached therein.

The upper part 302 has a pair of front guide plates 330 disposed at both sides of the narrow part 310 of the locking plate 304, a pair of back guide plates 332 disposed at both sides of the narrow part 313, and a top plate (retainer plate) 334 connected to the upper ends of the front and back guide plates 330, 332. The lower ends of the front and back guide plates 330, 332 are bent to form the mounting flanges 336. In each of the mounting flanges 336, a hole is formed at the center. The upper part 302 is fixed to the pulley container 300 such that screws 338 are threaded through the above holes into screw holes 340 on the upper surface of the pulley container 300.

The two coil springs 306 are placed between the top plate 334 and the locking plate 304. An elastic force of the coil springs 306 is applied to the locking plate 304 in the Y2 direction. When the alignment pins 212a to 212c come into contact with and push the locking plate 304, the coil springs 306 can be compressed to move the locking plate 304 in the Y1 direction. The locking plate 304 can be smoothly moved in the Y direction such that the narrow parts 310, 313 are guided by the front and back guide plates 330, 332. The two coil springs 306 are spaced away from each other in the longitudinal Z direction, whereby a balanced force can be applied to the locking plate 304 and the locking plate 304 can be smoothly moved in the Y direction.

The operation of the manipulator 10 having the above structure will be described below.

Figure 7:
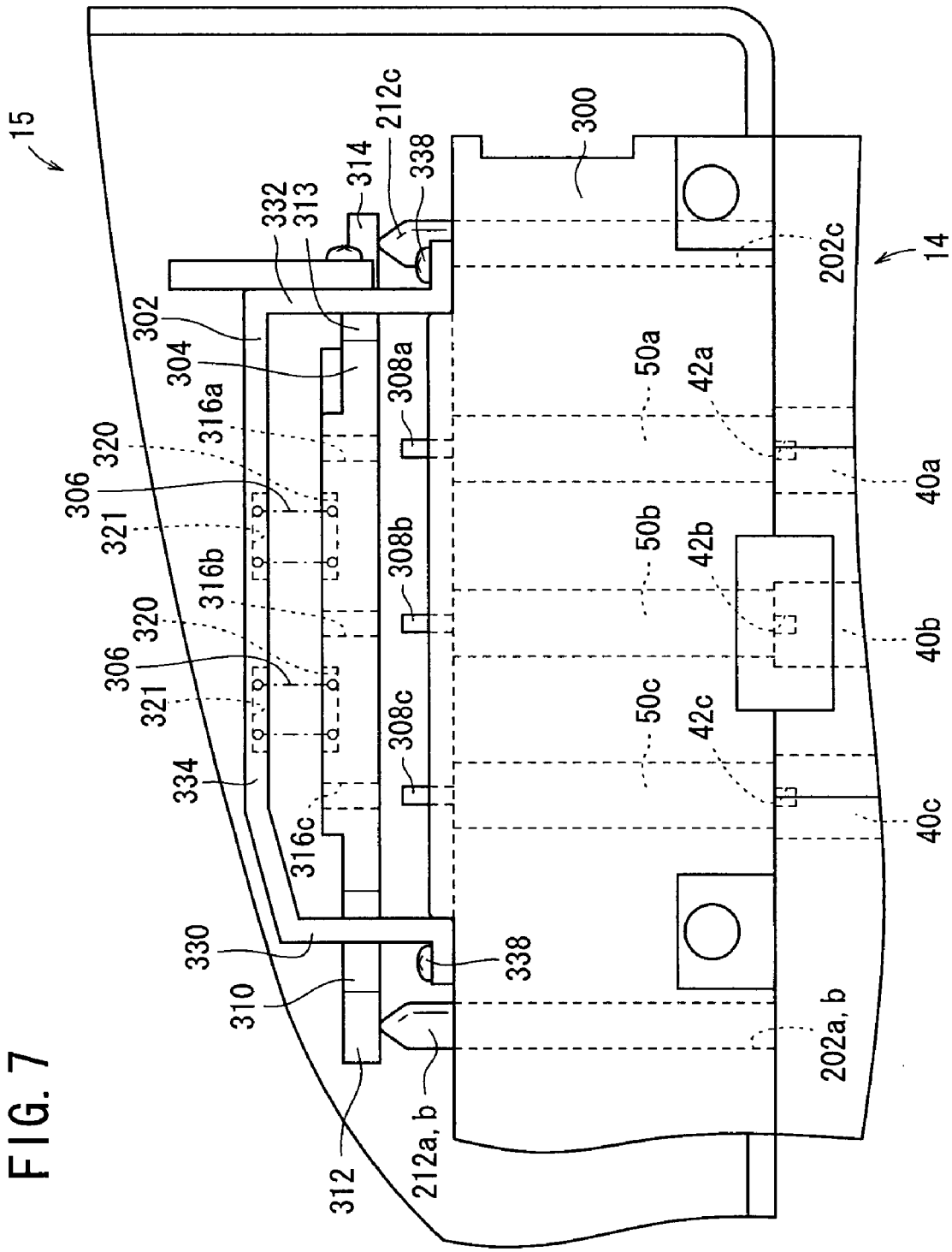
FIG. 7 is a side view of the connecting portion connected to the operation command unit.

First the working unit 16 is attached to the operation command unit 14 as shown in FIG. 7. When the connecting portion 15 is connected to the actuator block 30, the connecting portion 15 is moved in the Y2 direction such that the alignment pins 212a to 212c are inserted into the three mating holes 202a to 202c as shown in FIG. 4. The levers 206 of the engaging portions 210 are pressed outward due to the tapered ends and slides along the engaging pieces 200. Then, when the lower surface of the connecting portion 15 is brought into contact with the upper surface of the actuator block 30, the levers 206 return to the original positions due to the elastic force, and wedges 206a formed in the tapered ends of the levers 206 are engaged with the engaging pieces 200. When the connecting portion 15 has been attached and the levers 206 return to the original positions, suitable click and fitting noise are caused, whereby the operator can appropriately confirm the completion of the attachment.

At the time, the motors 40a to 40c in the operation command unit 14 are at the original points while the pulleys 50a to 50c in the working unit 16 are positioned at the original points by the locking plate 304, and thus the upper ends of the motors 40a to 40c are appropriately connected to the lower ends of the pulleys 50a to 50c.

As shown in FIG. 7, the upper ends of the three alignment pins 212a to 212c extend through the mating holes 202a to 202c, project from the upper surface of the pulley container 300, and are in contact with the lower surfaces of the first and second ends 312, 314. The coil springs 306 are compressed and the locking plate 304 is moved upward in this manner. Thus, the plate-shaped portions 308a to 308c formed at the upper ends of the pulleys 50a to 50c pass through the slits 316a to 316c in the locking plate 304, and the pulleys 50a to 50c is made rotatable with the motors 40a to 40c.

After the attachment of the working unit 16, in the controller 45, angles are calculated using the original point as a reference to accurately control the end working portion 12. Thus, the position of the attached operation command unit 14 is considered as the original point (0°), and the end working portion 12 is rotated in the roll or yaw direction and the gripper 60 is opened or closed in response to plus or minus input from the trigger lever 32 and the composite input part 34.

When a series of procedures are completed or the working unit 16 is interchanged with another one such as an electric knife, the working unit 16 is removed from the operation command unit 14. Before the removal, operator handles the switch 36 (see FIG. 1) to automatically return the motors 40a to 40c to the original point under the control of the controller 45. During or after the automatically returning step, the lighting state of the LED 29 (see FIG. 1) is changed by the controller 45. Specifically, the LED 29 is in the green lighting state during the normal operation, in the green blinking state during the automatically returning step, and in the non-lighting state after the returning step. The LED 29 is placed in a visible position, whereby the operator can easily confirm the return of the motors 40a to 40c to the original points.

After the return of the motors 40a to 40c are confirmed by observing the lighting state of the LED 29, the operator detaches the working unit 16 from the operation command unit 14.

Figure 8:
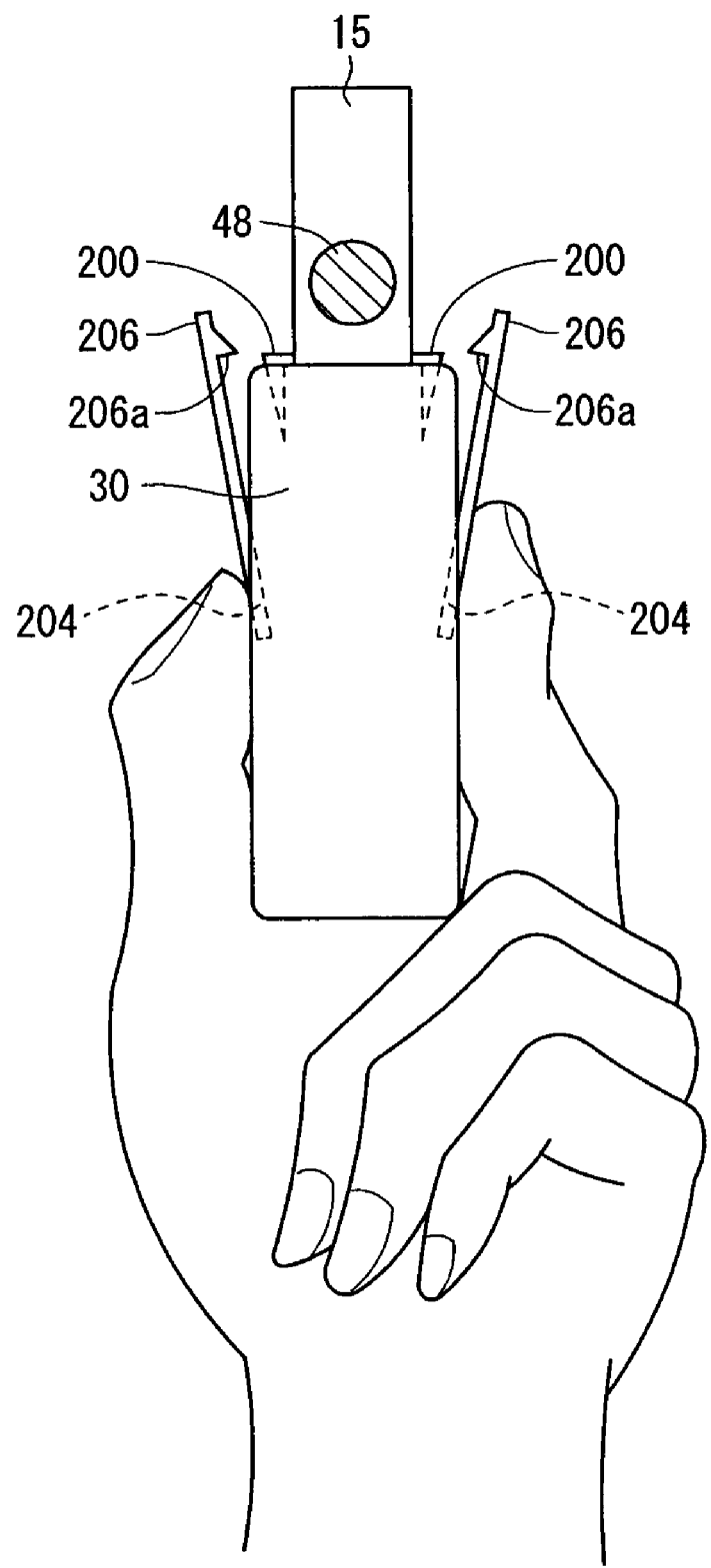
FIG. 8 is a front view of the manipulator, two operation surfaces being simultaneously pressed to remove the connecting portion from the actuator block.
Figure 9:
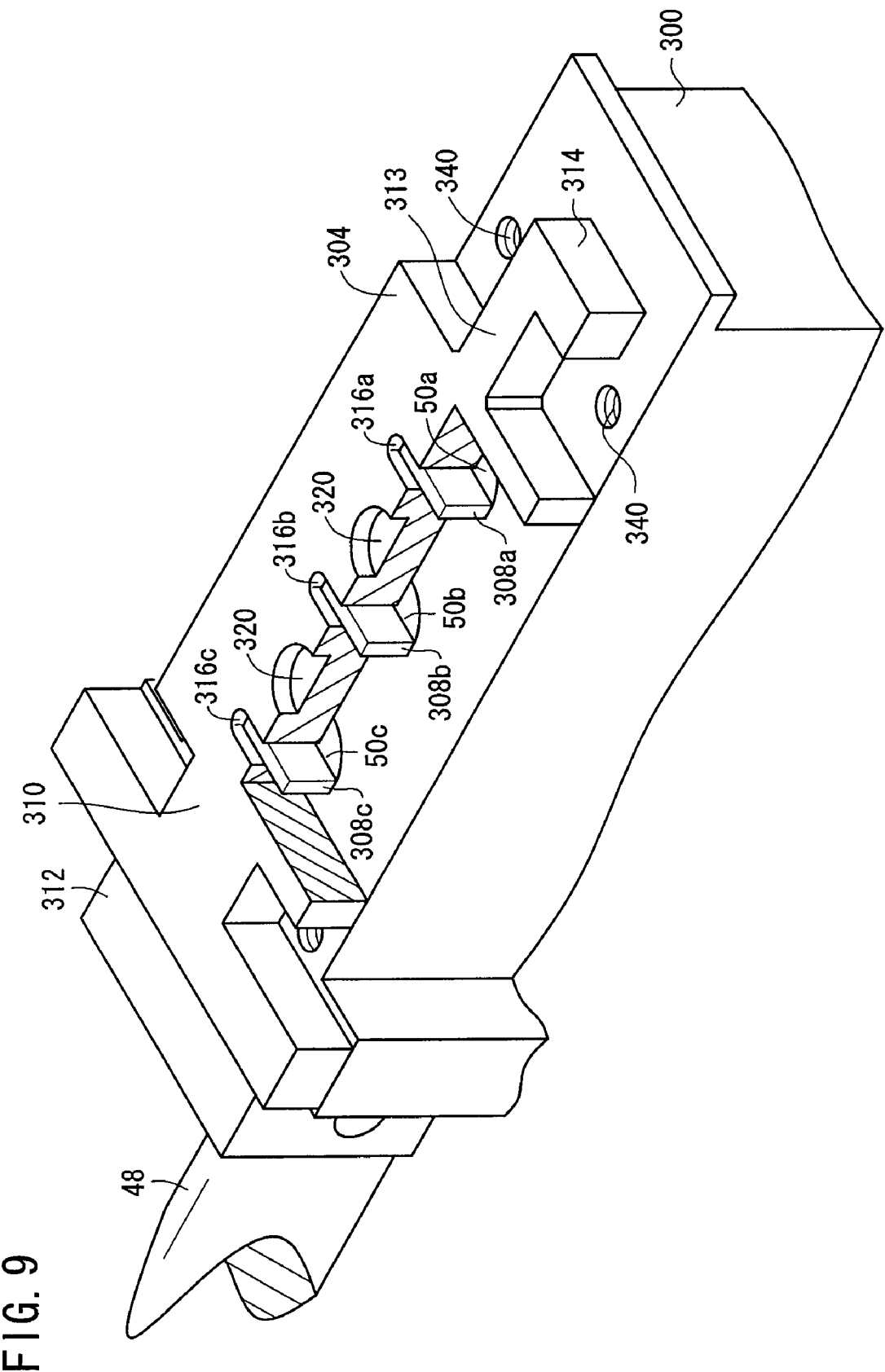
FIG. 9 is a partially sectional perspective view of a locking plate and a neighboring part, connected to the operation command unit.

As shown in FIG. 8, when the connecting portion 15 is detached from the actuator block 30, the levers 206 can be disengaged from the engaging pieces 200 such that the two operation surfaces 204 are simultaneously pressed against the elastic force to tilt the levers 206 outward. Then, the connecting portion 15 is moved upward to detach the working unit 16 from the operation command unit 14.

At this time, as shown in FIG. 6, the three alignment pins 212a to 212c are pulled out downward from the mating holes 202a to 202c and separated from the first and second ends 312, 314, so that the locking plate 304 is moved downward by the elastic force of the coil springs 306. Because the motors 40a to 40c are returned to the original points, the plate-shaped portions 308a to 308c of the pulleys 50a to 50c are arranged in the X direction in conjunction with the motors 40a to 40c (see FIG. 5), and engaged with the three slits 316a to 316c of the locking plate 304 (see FIG. 9). Therefore, the pulleys 50a to 50c can be prevented from rotating, the end working portion 12 can be kept at the original point, and the pulleys 50a to 50c can be precisely attached again to the motors 40a to 40c in the next operation.

As described above, in the medical manipulator 10 according to this embodiment, the locking member of the locking plate 304 is moved by the alignment pins 212a to 212c contained in the operation command unit 14, and is engaged with and disengaged from the plate-shaped portions 308a to 308c of the pulleys 50a to 50c. Thus, when the working unit 16 is separated from the actuator block 30, the plate-shaped portions 308a to 308c are engaged with the slits 316a to 316c of the locking plate 304 to prevent the pulleys 50a to 50c form rotating, and the end working portion 12 and the pulleys 50a to 50c are automatically locked at the positions corresponding to the original points.

When the working unit 16 is separated from the operation command unit 14, the locking plate 304 is elastically urged by the coil springs 306, and the plate-shaped portions 308a to 308c are held in fitting engagement with the slits 316a to 316c. When the working unit 16 is connected to the operation command unit 14, the locking plate 304 is pushed by the alignment pins 212a to 212c. Thus, the locking and unlocking can be automatically controlled without additional operation.

The alignment pins 212a to 212c can move the locking plate 304, and further can be fitted into the mating holes 202a to 202c to stably fix the pulley container 300. The structure is efficient in view of reducing the number of members.

The locking plate 304 has an elongate shape, and the coil springs 306 are spaced away from each other in the longitudinal direction, whereby a balanced force can be applied to the locking plate 304. The coil springs 306 are disposed between the top plate 334 and the locking plate 304, and the structure is efficient in space-saving.

The pulleys 50a to 50c and the locking plate 304 are engaged with each other through the plate-shaped portions 308a to 308c and the slits 316a to 316c, and the structure is simple and capable of reliably preventing the rotation of the pulleys 50a to 50c.

In the manipulator 10, when the working unit 16 is separated from the actuator block 30, the end working portion 12 and the pulleys 50a to 50c are automatically locked at the axial positions corresponding to the original points. However, it is preferred that they can be unlocked in the maintenance, etc.

Figure 10:
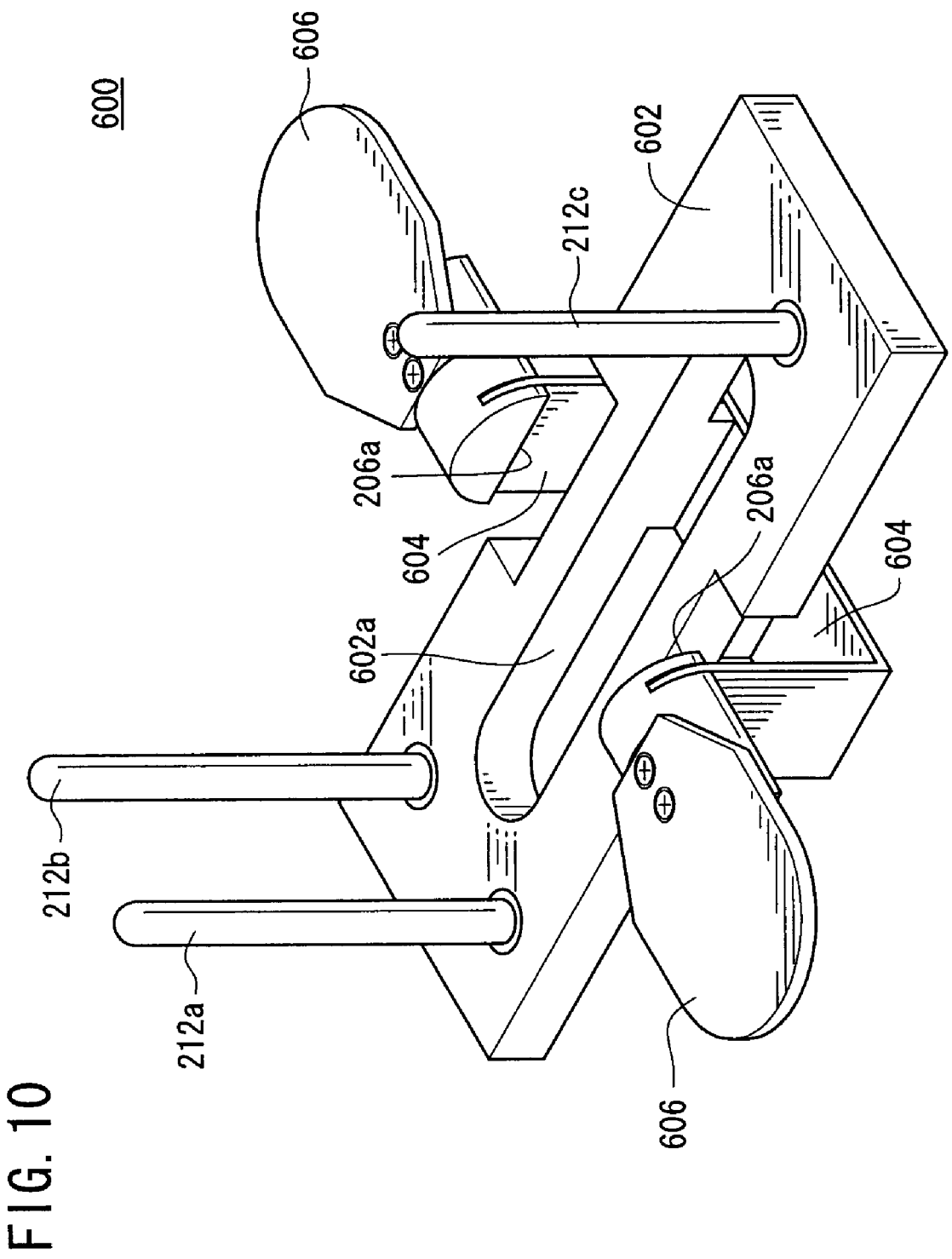
FIG. 10 is a perspective view of a jig.

When the working unit 16 is separated from the actuator block 30, a jig 600 shown in FIG. 10 may be used for unlocking the end working portion 12 and the pulleys 50a to 50c. The jig 600 has a base plate 602, a pair of right and left leaf springs 604, and knobs 606 disposed on the upper portions of the leaf springs 604.

The base plate 602 is in the same shape as the actuator block 30 and has a center hole 602a and three alignment pins 212a, 212b, 212c. The alignment pins 212a to 212c of the base plate 602 have the same arrangement, shape, and length as above (see FIG. 3). The center hole 602a is formed in order to manually control the pulleys 50a to 50c using a specific jig (not shown). The leaf springs 604 have an L shape, and project rightward and leftward from protrusions formed on the lower surface of the base plate 602, and are bent upward. The knobs 606 project rightward and leftward, and the wedges 206a are formed on the inner sides thereof. By handling the knobs 606, the leaf springs 604 can be elastically deformed, and the wedges 206a can be engaged with and disengaged from the engaging pieces 200 (see FIG. 4).

By connecting the jig 600 to the connecting portion 15, the locking plate 304 (see FIG. 7) can be pushed up by the alignment pins 212a, 212b, 212c, and the end working portion 12 and the pulleys 50a to 50c can be unlocked. In this manner, the working unit 16 can be more easily maintained and washed (the working unit 16 can be washed while driving). Further, when emergently stopped, the working unit 16 can be unlocked even in the vicinity of the original point, and can be manually driven and removed.

The connecting portion 400 according to a first modification example of the connecting portion 15 will be described below with reference to FIG. 11. The connecting portion 400 has a locking member 404 tiltably supported by two posts 402, and a torsion spring 406 for applying an elastic force to lay down the locking member 404. The locking member 404 functionally corresponds to the above-described locking plate 304. The locking member 404 is disposed on the upper surface of a pulley container 300, and has a bar 408 extending in the Z direction, three branches 410a, 410b, 410c extending laterally from the bar 408, and a cam follower 412 formed at one end thereof. The branches 410a to 410c functionally correspond to the above described slits 316a to 316c.

Figure 11:
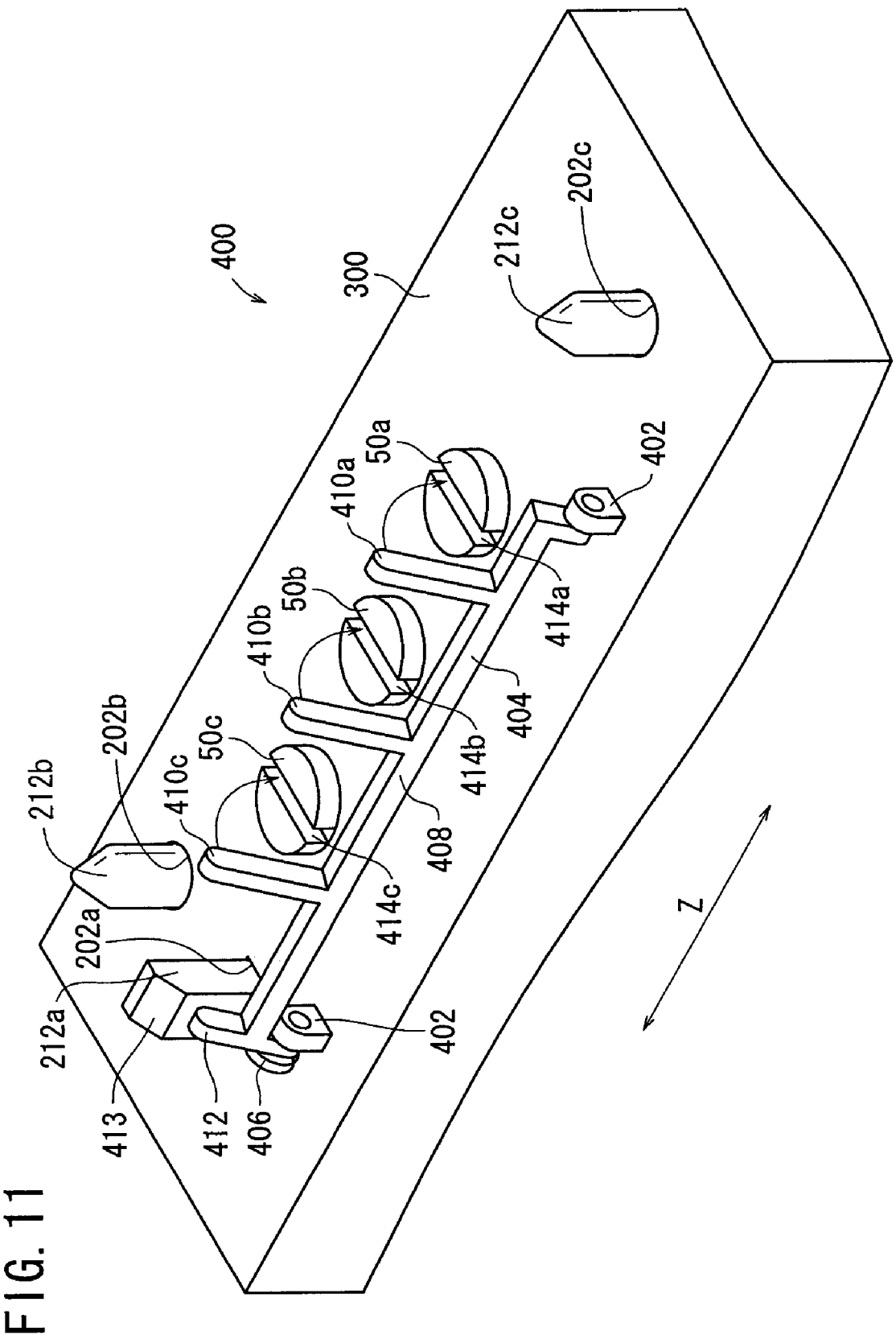
FIG. 11 is a perspective view of a connecting portion according to a first modification example.

As shown in FIG. 11, an oblique cam face 413 is formed on the upper end of an alignment pin 212a, and the cam follower 412 can be pushed up by the alignment pin 212a through a mating hole 202a, to open the locking member 404 obliquely. Grooves (engaging portions) 414a to 414c are formed on the upper surfaces of pulleys 50a, 50b, 50c in the diameter direction. The grooves 414a to 414c functionally correspond to the above described plate-shaped portions 308a to 308c, and are slightly wider than the branches 410a to 410b.

When the connecting portion 400 is separated from the operation command unit 14, the locking member 404 is laid down on the upper surface of the pulley container 300 due to the torsion spring 406, and the branches 410a to 410c are fitted into the grooves 414a to 414c to prevent the rotation of the pulleys 50a to 50c. On the other hand, when the connecting portion 400 is removed from the operation command unit 14, the cam follower 412 is pushed up by the alignment pins 212a to move the locking member 404, and thereby the branches 410a to 410c are separated from the grooves 414a to 414c. The pulleys 50a to 50c are made rotatable in this manner.

The connecting portion 400 of this modification example has the same effects as the above connecting portion 15.

A connecting portion 500 according to a second modification example of the connecting portion 15 will be described below with reference to FIGS. 12 to 14.

The connecting portion 500 has three locking mechanisms 502, a body 504, a front support 506, a rear support 508, an upper electrode 510, and a cleaning pipe 512, through which a cleaning liquid flows.

The locking mechanisms 502 are disposed below pulleys 50a to 50c, to prevent the rotation of the pulleys 50a to 50c individually.

Figure 12:
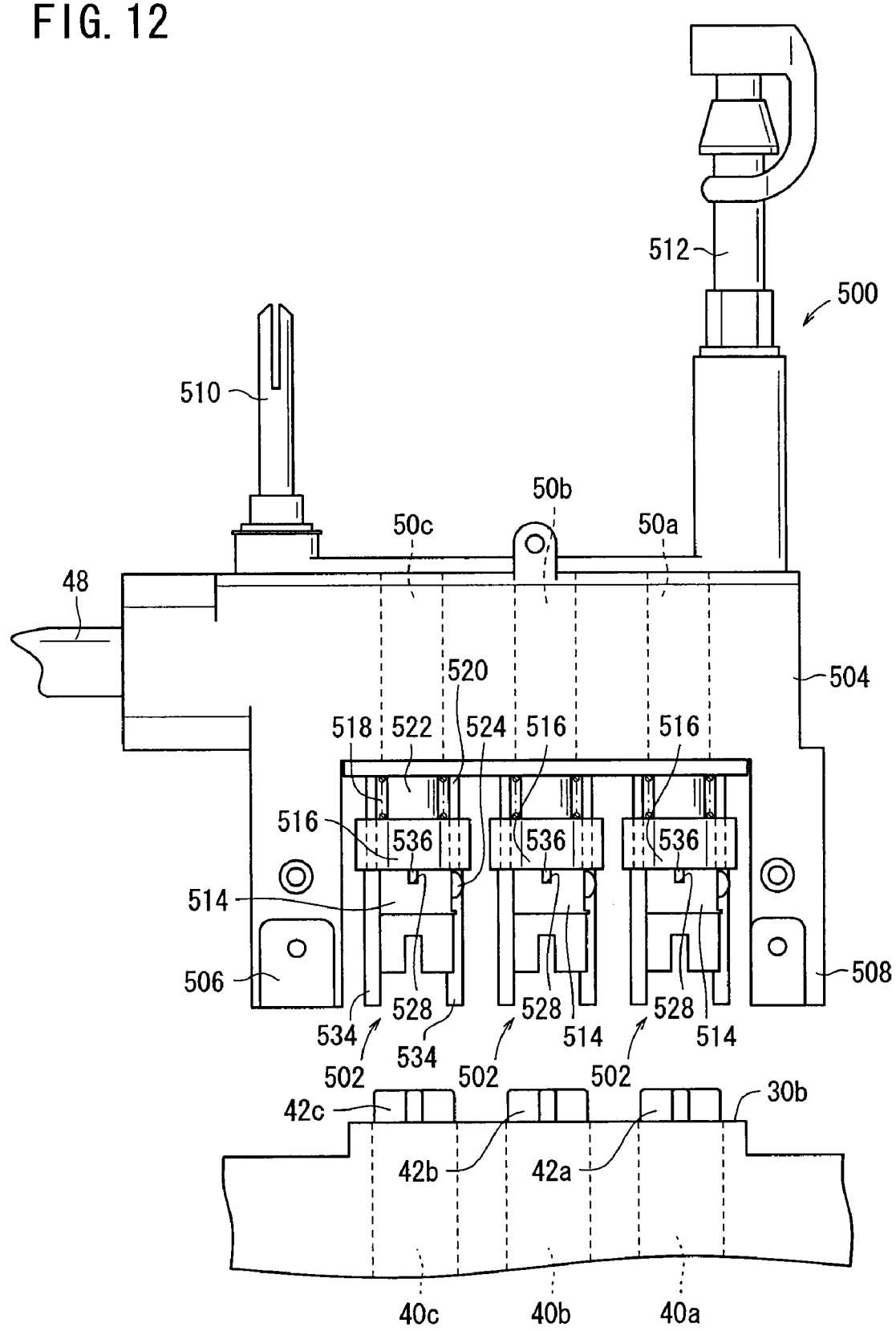
FIG. 12 is a side view of a connecting portion according to a second modification example.
Figure 13:
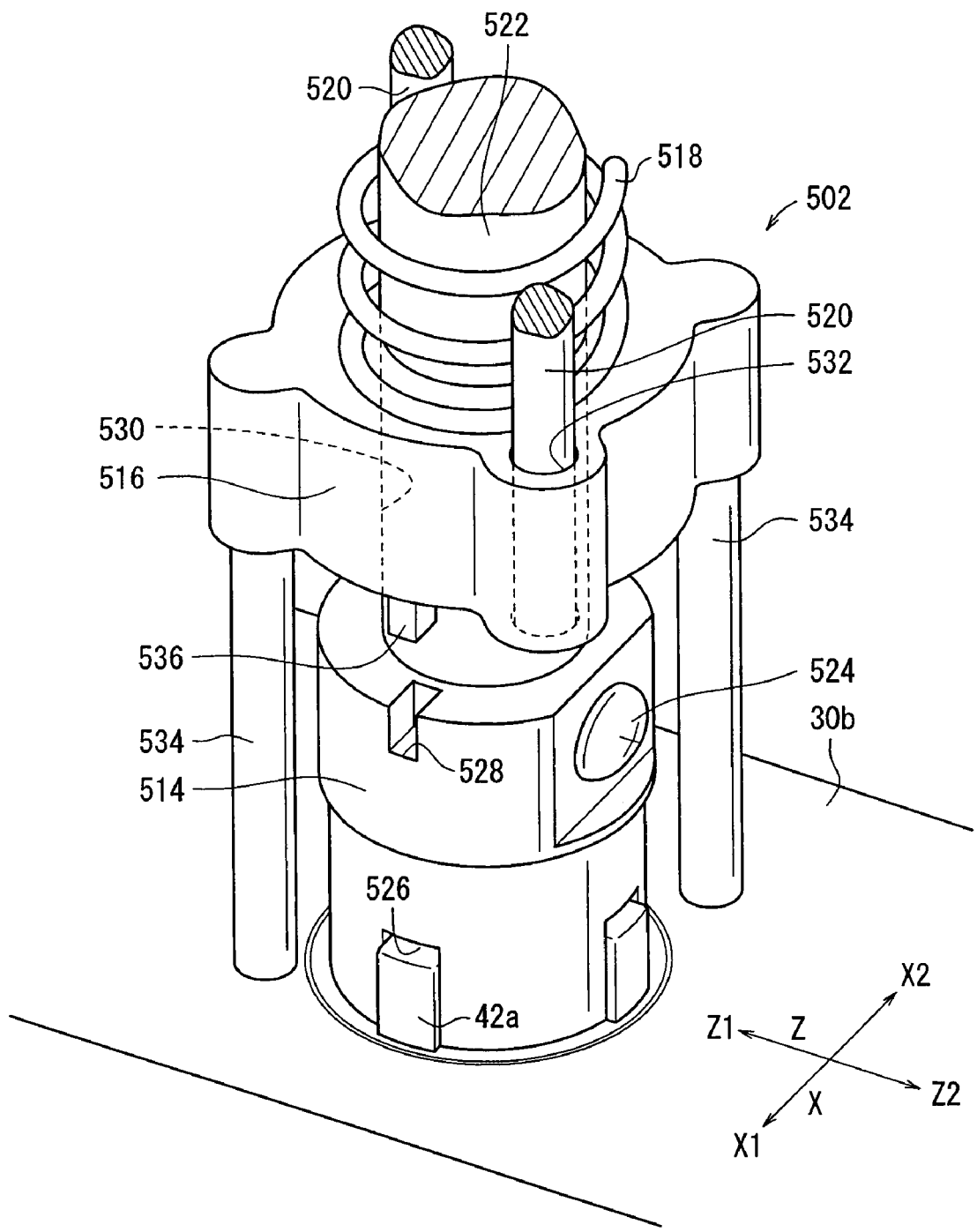
FIG. 13 is a partially sectional perspective view of a locking mechanism.

As shown in FIGS. 12 and 13, each of the locking mechanisms 502 has a link 514, a locking member 516, a spring 518, and a pair of guide rods 520. The guide rods 520 project downward from the body 504.

Each of the links 514 is fixed by a screw 524 to the lower end of a cylinder 522 on the lower part of the pulley 50a to 50c, and is rotated in conjunction with the pulley 50a to 50c. The links 514 each have a cross-shaped recess 526 engaged with a rotary shaft 42a to 42c of a motor 40a to 40b on the lower surface, and each have a notch 528 formed on the upsides. The cross-shaped recesses 526 are in the X and Y directions when the pulleys 50a to 50c are in the axial positions corresponding to the original points. The rotary shafts 42a to 42c have cross-shaped projections corresponding to the cross-shaped recesses 526, and the projections are in the X and Y directions when the motors 40a to 40c are at the original points. The notches 528 are in the X1 direction when the pulleys 50a to 50c are in the axial positions corresponding to the original points.

The locking members 516 can be up-and-down-moved along the cylinders 522 between the links 514 and the body 504, and each have a center hole 530 in which the cylinder 522 is inserted, a pair of guide holes 532 in which the guide rods 520 are inserted, a pair of downward rods 534, and an engaging piece 536 that is fitted into the notch 528. The guide holes 532 are disposed symmetrically, the rods 534 are disposed symmetrically, and the guide holes 532 and the rods 534 are disposed at angular intervals of 90°. The engaging piece 536 is disposed in the X1 direction, and slightly projects downward. The spring 518 is disposed between the locking member 516 and the body 504, and acts to elastically urge the locking member 516 downward. The guide rods 520 act to guide the locking member 516 upward and downward, and to prevent the rotation of the locking member 516.

In the locking mechanisms 502 of the connecting portion 500, the locking members 516 are pushed downward by the springs 518 and brought into contact with the links 514 when the working unit 16 is separated from the actuator block 30. In this case, when the motors 40a, 40b, 40c are positioned at the original points, the engaging pieces 536 of the locking members 516 are engaged with the notches 528, to lock the pulleys 50a, 50b, 50c.

Figure 14:
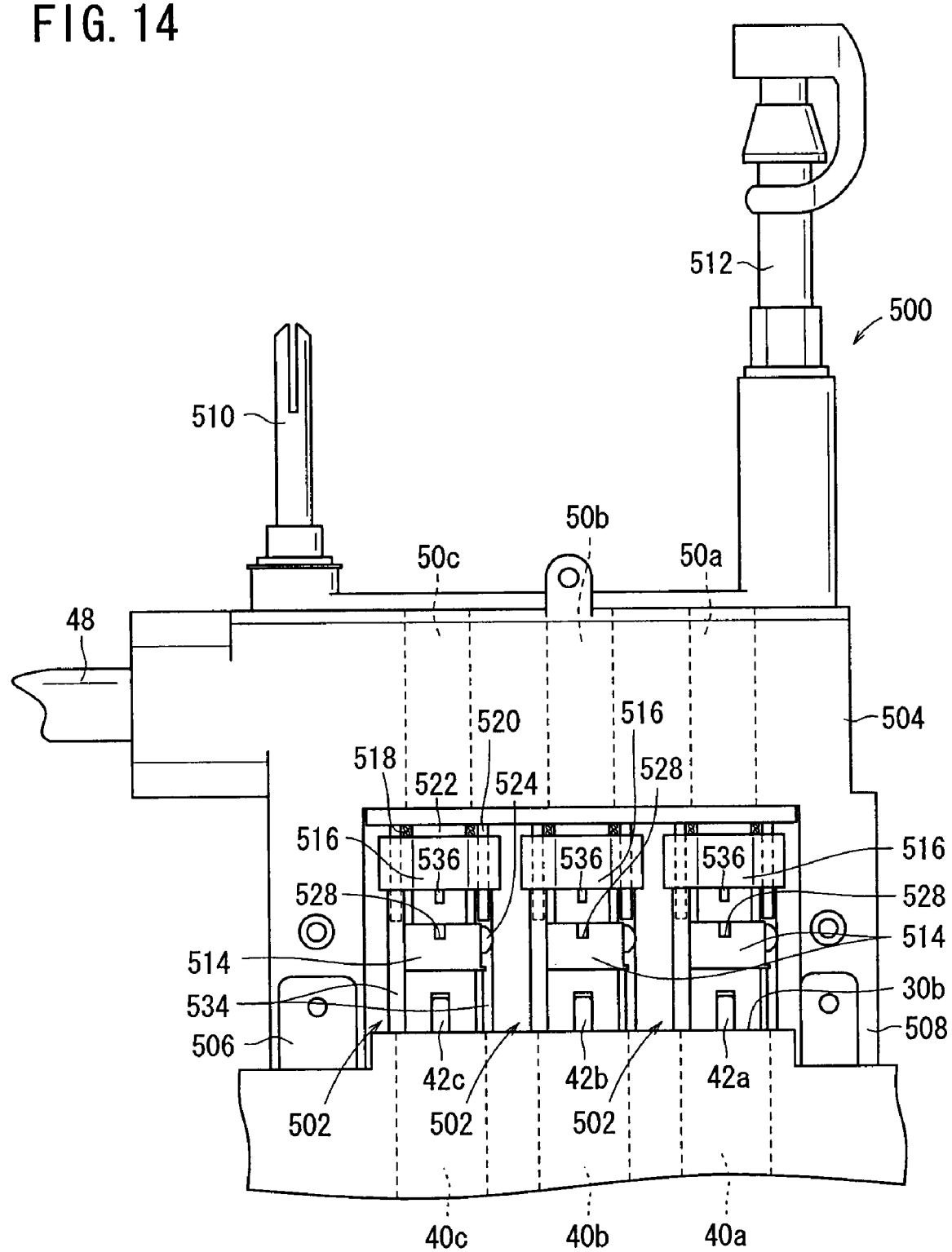
FIG. 14 is a side view of the connecting portion according to the second modification example.

As shown in FIGS. 13 and 14, when the working unit 16 is connected to the actuator unit 30, the lower surfaces of the rods 534 are brought into contact with the upper surface 30b of the actuator block 30 (a part of the actuator unit), and the springs 518 are compressed, thereby pushing up the locking members 516. Thus, the engaging pieces 536 are separated from the notches 528, and the pulleys 50a, 50b, 50c are made rotatable in conjunction with the motors 40a, 40b, 40c. The locking mechanisms 502 are disposed between the front and rear supports 506, 508, and thereby cannot be carelessly handled.

Then, a medical manipulator system 1100 according to a second embodiment will be described below. First, components of the medical manipulator system 1100 and the corresponding components of the above-mentioned manipulator 10 will be described.

The main components of the medical manipulator system 1100: a manipulator 1102(a), a control unit 1104(b), a surgical instrument 1106(c), a surgical instrument control unit 1112(d), a surgical tool controller 1107(e), a surgical tool 1122(f), a shaft 1116(g), a handle 1110(h), a button 1114(i), a cable conduit 1115(j), a motor 1212(k), a locking plate 1402 (l), a drive assembly 1204 and a surgical instrument connector 1400(m), a spring 1401(n), a surgical instrument control unit connector 1410(o), and a notched aperture 1800(p), correspond respectively to the components of the manipulator 10: the manipulator 10(a), the controller 45(b), the working unit 16(c), the actuator block 30(d), the connecting portion 15(e), the end working portion 12(f), the connecting shaft 48(g), the grip handle 26(h), the trigger lever 32(i), the cable 62(j), the motor 40a to 40c(k), the locking plate 304(l), the pulley 50a to 50c(m), the coil spring 306(n), the motor rotary shaft 42a to 42c(o), and the slit 316a to 316c(p). The signs in the parentheses are shown in order to easily compare the corresponding components.

Figure 15:
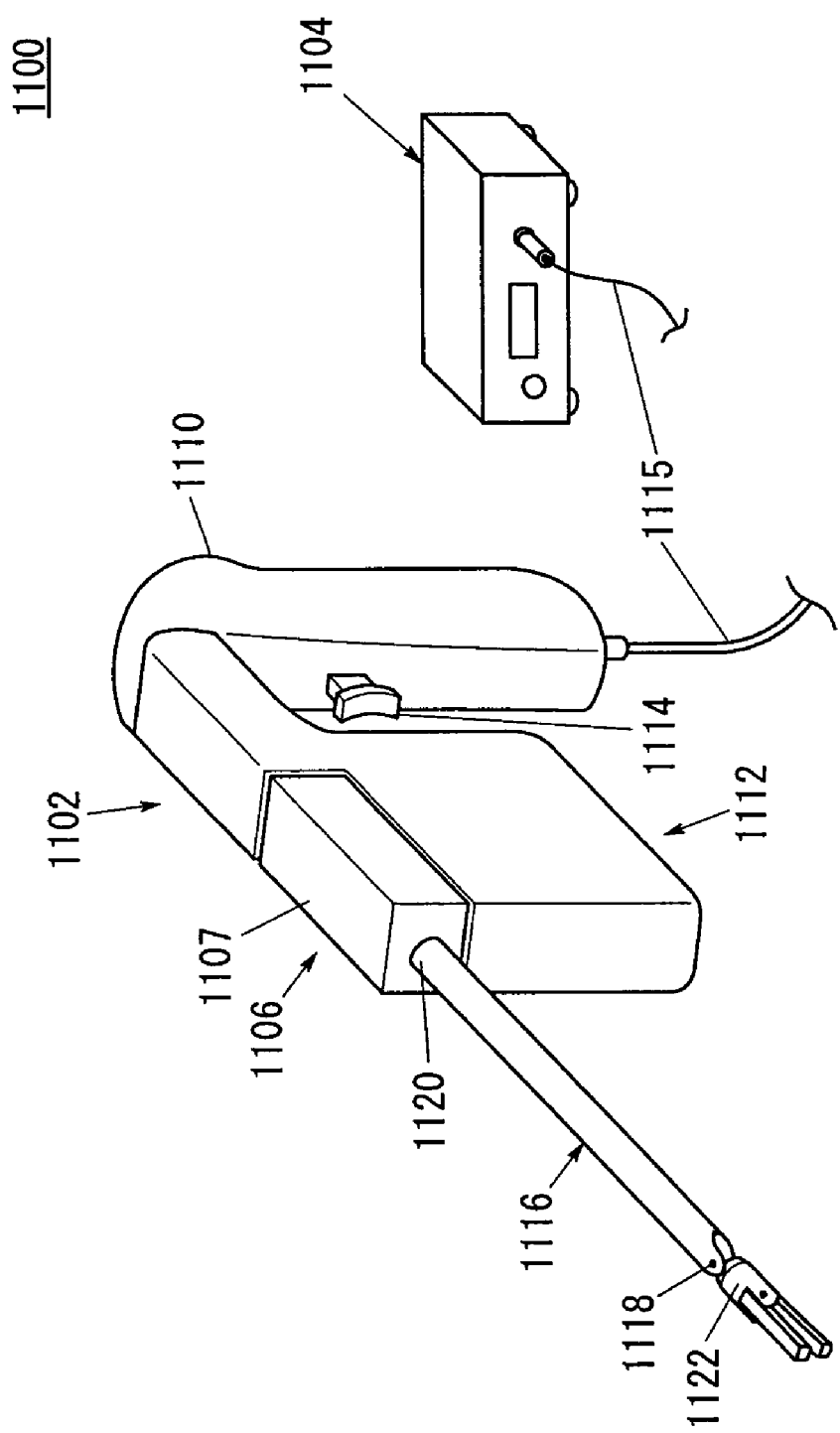
FIG. 15 is a perspective view of a robotic surgical device according to a second embodiment of the present invention.

With reference to FIG. 15, a perspective view of a manipulator system 1100 for medical use according to a second embodiment is shown. The manipulator system 1100 may include a manipulator for medical use 1102 and a control unit 1104. The manipulator 1102 may include a surgical instrument 1106 and a surgical instrument control unit (actuator unit) 1112. The surgical instrument 1106 may include a surgical tool controller 1107, a surgical tool 1122, and a shaft 1116. The shaft 1116 has a first end 1118 and a second end 1120 opposite to the first end 1118. The surgical tool 1122 mounts to the first end 1118 of the shaft 1116 using a variety of mechanisms as known to those skilled in the art both now and in the future. The surgical tool controller 1107 mounts to the second end 1120 of the shaft 1116 using a variety of mechanisms as known to those skilled in the art both now and in the future.

As used in this disclosure, the term "mount" includes join, engage, unite, connect, associate, insert, hang, hold, affix, attach, fasten, bind, paste, secure, bolt, screw, rivet, solder, weld, and other like terms.

The surgical instrument control unit 1112 may include a handle 1110 which a surgeon can maneuver and manipulate to perform minimally invasive surgical procedures using the surgical tool 1122. The handle 1110 may include a variety of control structures that may be rotated, depressed, toggled, etc. to indicate the desired movement of the surgical tool 1122.

For example, the handle 1110 includes a button 1114 that the surgeon may depress to cause opening and closing of the surgical tool 1122. The surgical instrument control unit 1112 is electrically connected to a control unit 1104 through cables within a cable conduit 1115.

The control unit 1104 sends and receives electrical signals through cable conduit 1115 to/from the surgical instrument control unit 1112, which controls movement of the surgical tool 1122 through a coupling with the surgical tool controller 1107. For example, control software receives electrical signals indicating movement of the button 1114 and transforms the movement to appropriate signals for an electromechanical system to effect movement of the surgical tool 1122. The electrical signals may be analog or digital. The control unit 1104 may further convert angle measurements received from transducers mounted in the handle 1110 to determine control commands that are transmitted to the surgical instrument control unit 1112 which controls the surgical tool 1122.

Figure 16:
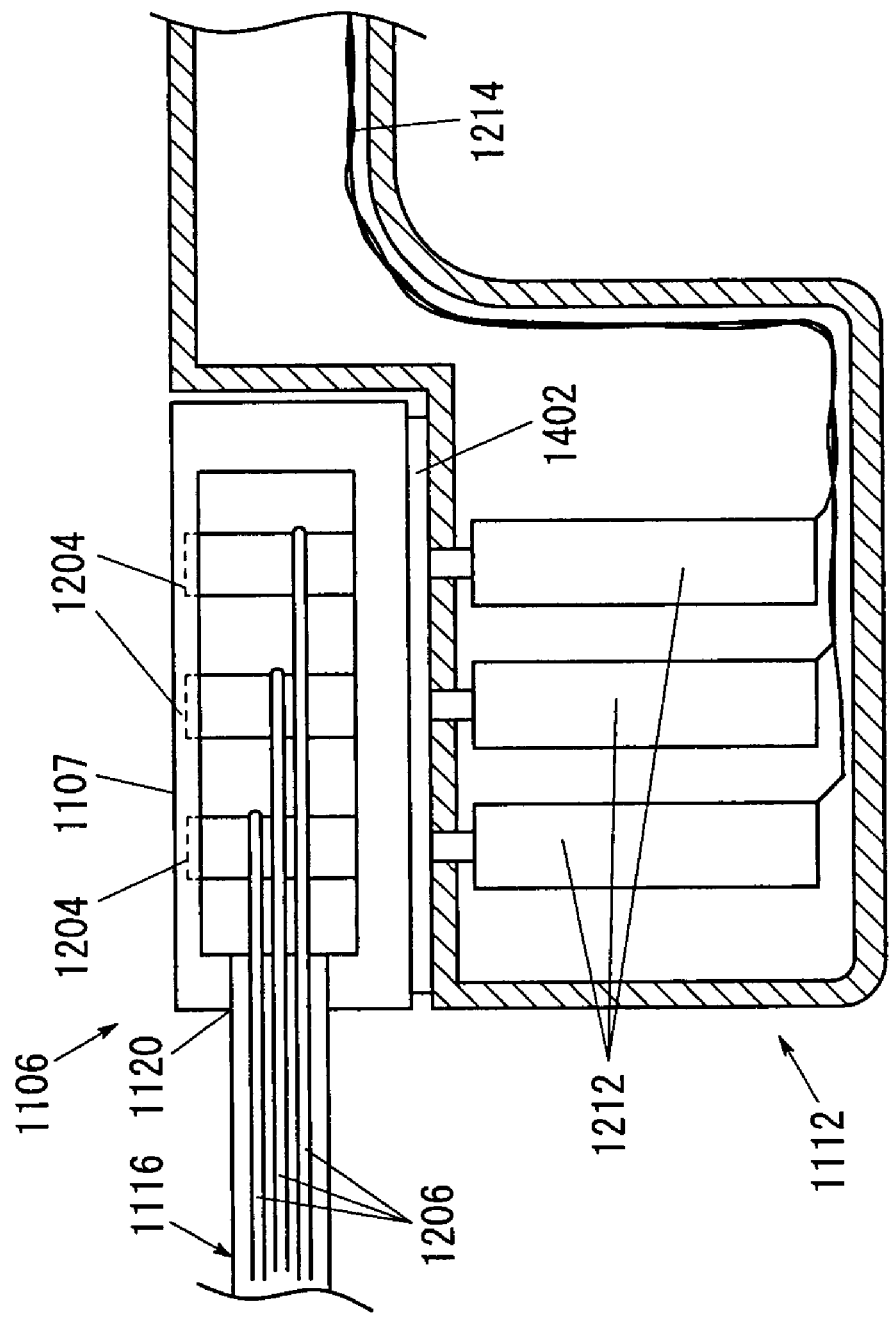
FIG. 16 is a cross-sectional view of a robotic surgical instrument control unit according to the second embodiment.

With reference to FIG. 16, the surgical tool controller 1107 may include a plurality of drive assemblies 1204 and a plurality of wires 1206. In general, the shaft 1116 includes an elongate tube through which the plurality of wires 1206 extend. The plurality of wires 1206 operably couple the surgical tool 1122 shown with reference to FIG. 15 with the surgical tool controller 1107. The surgical tool 1122 may be of many different types including devices specifically designed for cutting, scraping, suturing, grasping, etc.

With further reference to FIG. 16, the surgical instrument control unit 1112 may include a plurality of motors 1212 and a plurality of control electrical cables 1214 mounted within the surgical instrument control unit 1112.

The control unit 1104 shown with reference to FIG. 15 receives transducer (i.e., button 1114) measurements detected using transducers mounted in the handle 1110 shown with reference to FIG. 15. The control unit 1104 interprets the movement and provides control commands to the plurality of motors 1212 through the plurality of control electrical cables 1214. The plurality of motors 1212 engage with the plurality of the drive assemblies 1204 at a plurality of engagement points to physically connect the surgical instrument control unit 1112 to the surgical instrument 1106. The plurality of drive assemblies 1204 include mechanical components that translate commands from the control unit 1104 into mechanical movement of the surgical tool 1122 shown with reference to FIG. 15. For example, the plurality of motors 1212 create rotational torque that rotates the plurality of drive assemblies 1204. The rotation of the plurality of drive assemblies 1204 causes translational movement of the plurality of wires 1206, which in turn cause movement of the surgical tool 1122 shown with reference to FIG. 15. As described in more detail with reference to FIGS. 18 and 19, the surgical tool 1122 is only able to move when a locking plate 1402 is in an unlocked position.

Figure 17:
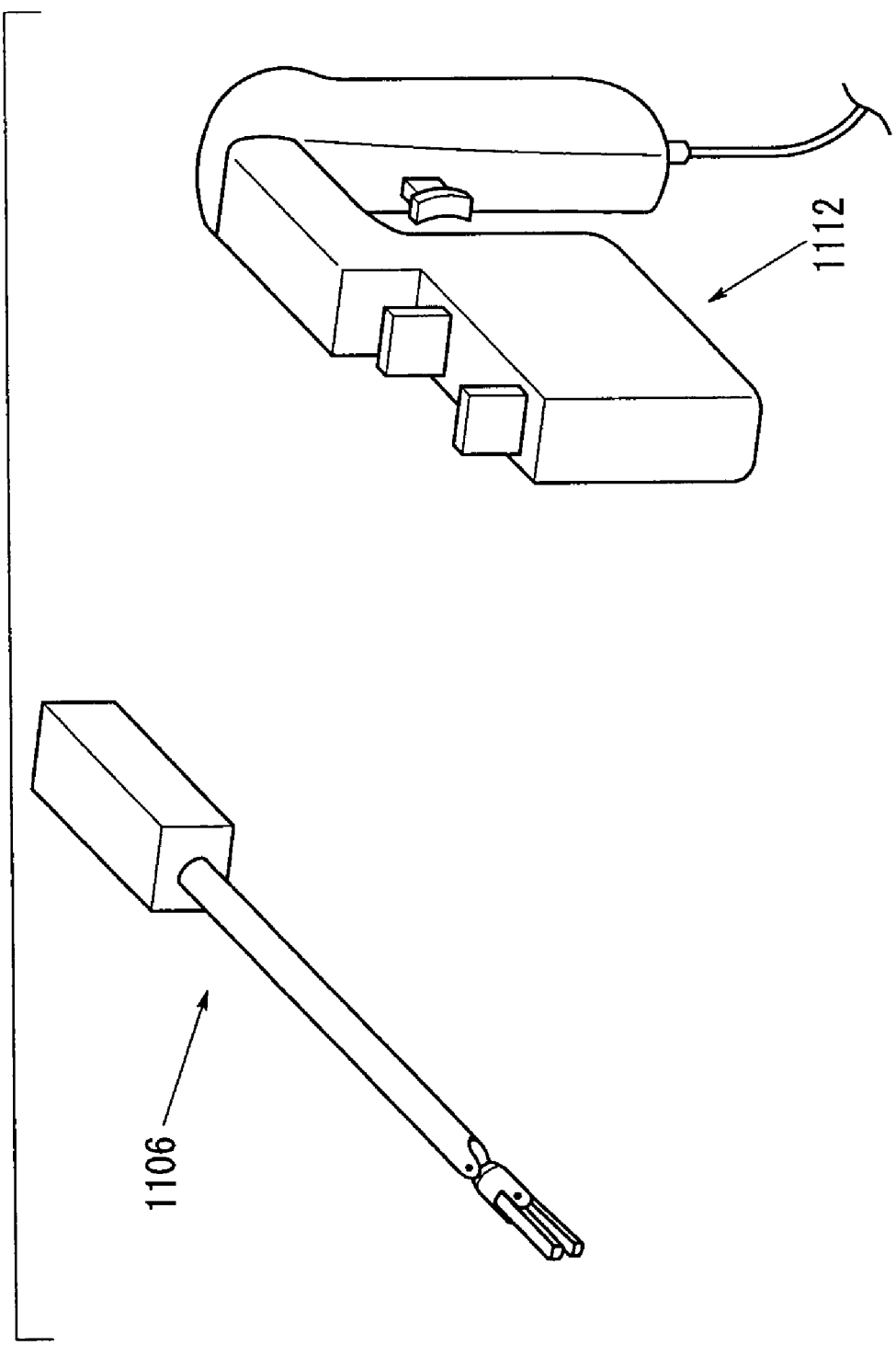
FIG. 17 is a perspective view of a surgical instrument detached from the control unit according to the second embodiment.

With reference to FIG. 17, the surgical instrument 1106 and the surgical instrument control unit 1112 are shown entirely disengaged from one another. The surgical instrument 1106 is removable from the surgical instrument control unit 1112 such that a variety of surgical instruments may be easily and quickly interchanged. Interchangeability saves time and eliminates the need for a separate surgical device devoted to each surgical instrument or tool.

Figure 18:
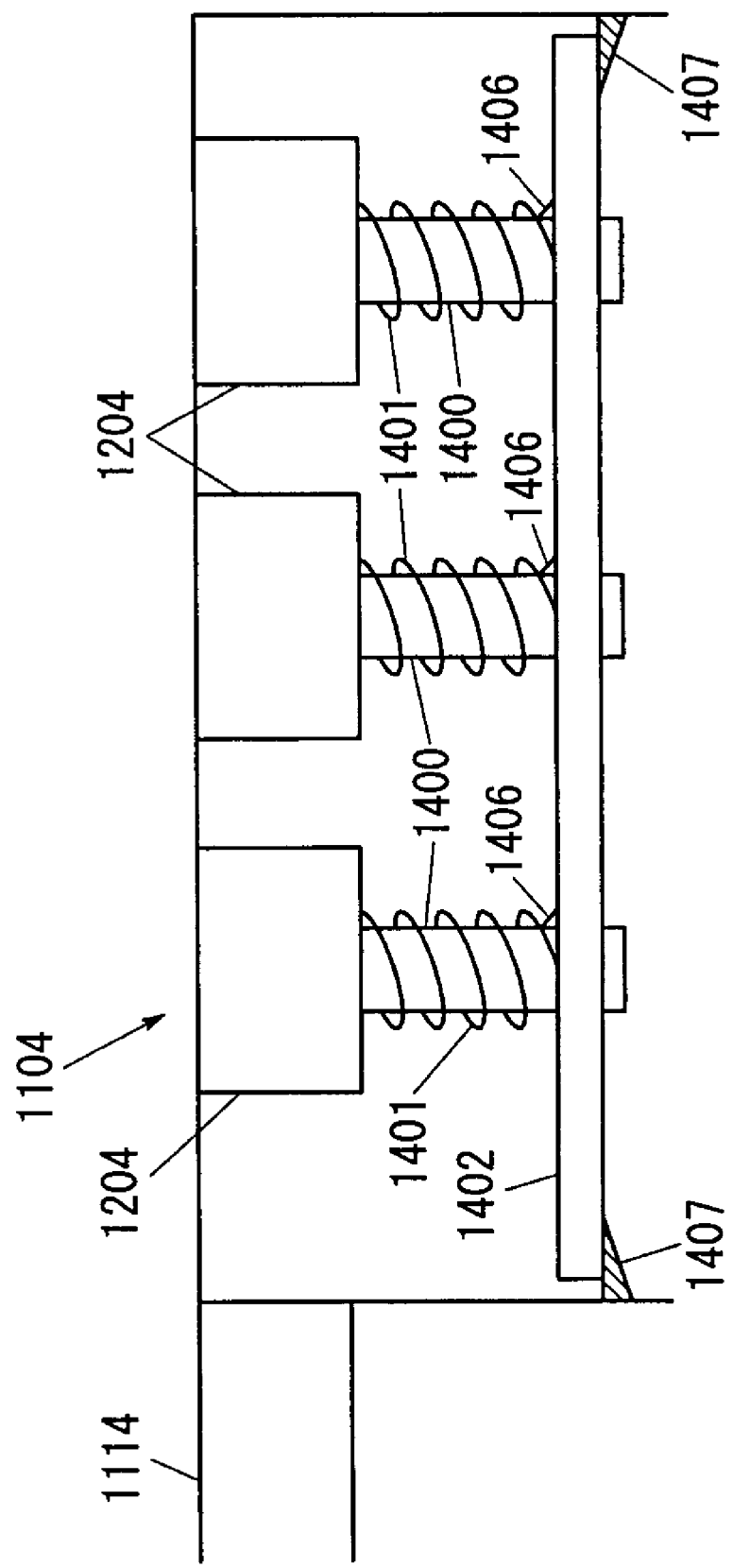
FIG. 18 is a cross-sectional view of a locking plate in a locked position according to the second embodiment.

With reference to FIG. 18, the surgical instrument 1106 is shown disengaged from the surgical instrument control unit 1112. The surgical instrument connectors (rotators) 1400 extend from each of the drive assemblies 1204. Springs 1401 urge the locking plate 1402 downward towards protrusions 1407.

Locking protrusions (non-circular portions) 1406 (partially hidden from view) are mounted to and extend from each of the surgical instrument connectors 1400. The locking plate 1402, which is illustrated in a locked position in FIG. 18, interacts with the locking protrusions 1406 to prevent rotation of the surgical instrument connectors 1400. Thus, the drive assemblies 1204 are prevented from rotating and the surgical tool 1122 cannot be controlled while the locking plate 1402 is in a locked position (first position).

Figure 19:
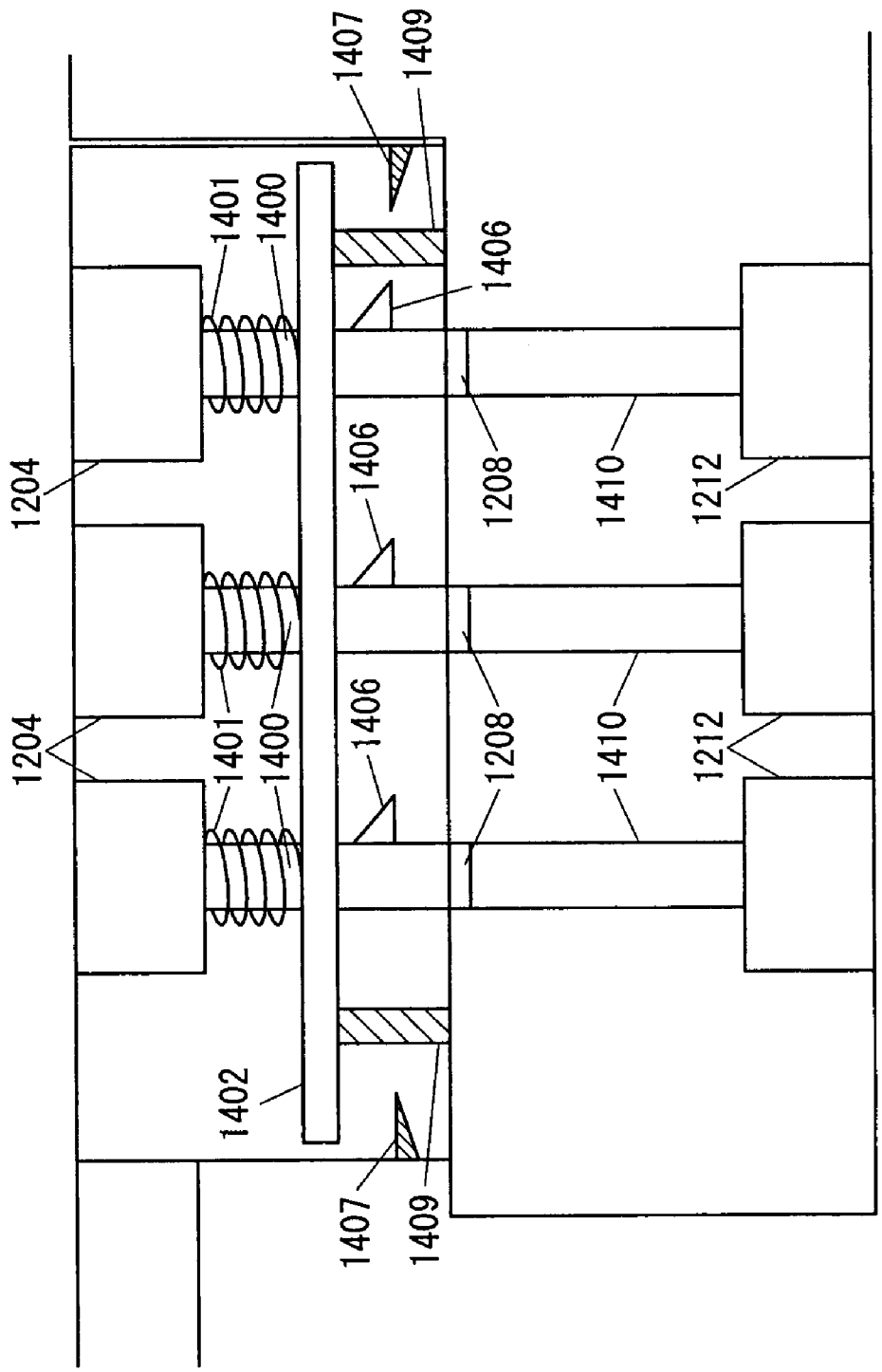
FIG. 19 is a cross-sectional view of the locking plate in an unlocked position, the surgical instrument being engaged with the control unit, according to the second embodiment.

With reference to FIG. 19, the surgical instrument 1106 is shown engaged with the surgical instrument control unit 1112. FIG. 19 illustrates the locking plate 1402 in an unlocked position. Unlocking protrusions 1409 urge the locking plate towards the drive assembly 1204 against the springs 1401. With the locking plate 1402 in the unlocked position (second position), the locking protrusions 1406 are fully clear of the locking plate 1402 and the motors 1212 are able to rotate the surgical instrument control unit connectors (rotary shaft) 1410 which in turn rotate the surgical instrument connectors 1400 and the drive assemblies 1204, enabling the surgical tool 1122 to be controlled.

Figure 20:
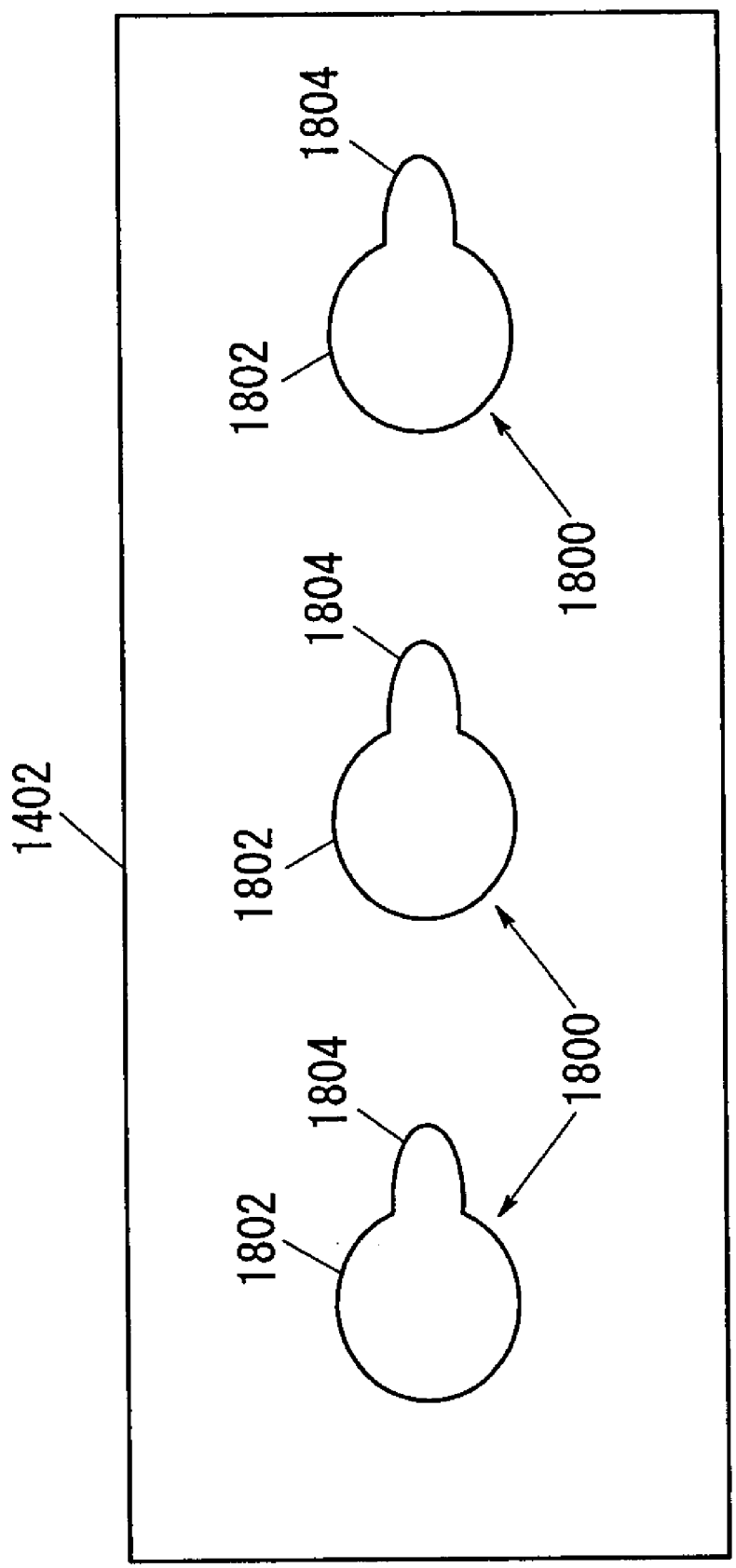
FIG. 20 is a front view of the locking plate according to the second embodiment.

FIG. 20 is a top view of the locking plate 1402. The locking plate 1402 contains notched apertures (engaging hole) 1800 composed of apertures 1802 and notches 1804. The notched apertures 1800 allow the locking plate 1402 to move vertically with respect to the surgical instrument connectors 1400 and the surgical instrument control unit connectors 1410. The apertures 1802 are circular in shape such that the surgical instrument connectors 1400 and the surgical instrument control unit connectors 1410 can pass through the locking plate 1402.

In alternative embodiments, the apertures can be shaped to mate with the surgical instrument connector, the surgical instrument control unit connector, or both. In one embodiment, the surgical instrument connector can have a cross-shaped protrusion (male end) extending therefrom. The cross-shaped protrusion can pass through a cross-shaped, notched aperture in the locking plate and mate with a cross-shaped aperture at the end of the surgical instrument control unit connector. Alternatively, the male and female roles of the surgical instrument connector and surgical instrument control unit connector can be reversed. In an alternative embodiment, the aperture in the locking plate and the male/female counterparts of the surgical instrument connector and surgical instrument control unit connector can be any shape including, but not limited to a star, cross, triangle, circle, ellipse, rectangle, polygon, etc.

The notches 1804 are elliptical in shape such that the locking protrusions 1406 can pass through the locking plate 1402. When the locking plate 1402 is in a locked position as illustrated with reference to FIG. 18, the locking protrusions 1406 fit within the notches 1804 to prevent rotation. When the locking plate 1402 is in an unlocked position as illustrated with reference to FIG. 19, the locking protrusions 1406 are clear of the notches 1804 and rotation is enabled. The notches and locking protrusions can be of the same shape or of different shapes, depending on the embodiment.

Though the above-described manipulator 10 is intended for medical use, the application is not limited to medical use. The manipulator of the present invention can be suitably used, for example, in repairing a narrow portion of an energy device, etc. or in a remote operation mechanism for operating a patient from a distance using a telecommunication means, etc.

Figure 21:
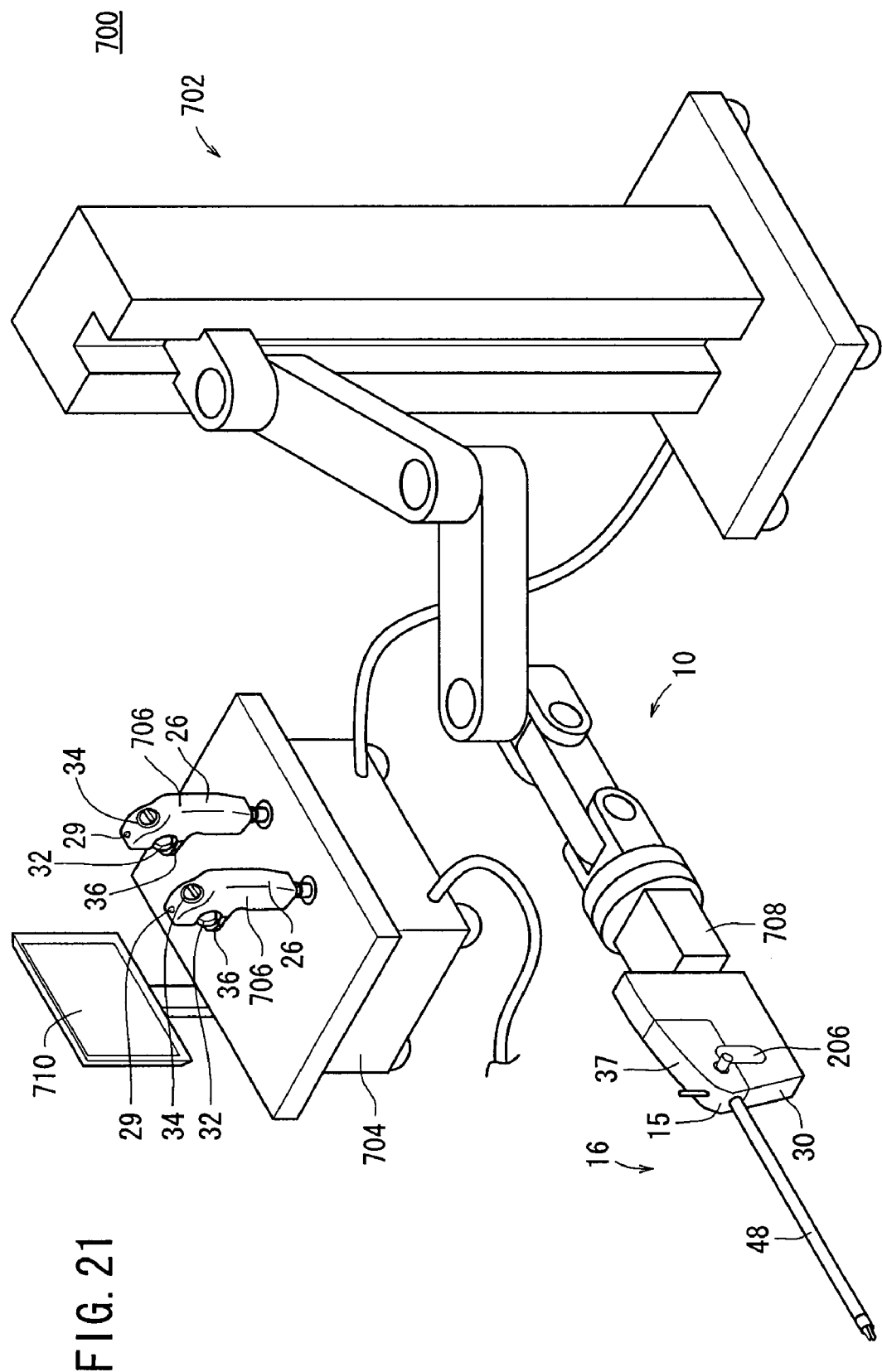
FIG. 21 is a schematic perspective view of a surgical robotic system having the working unit connected to a distal end of a robotic arm.

Though the above-described working unit 16 is connected to the operation command unit 14 handled by a human hand, the working unit can be used, for example, in a surgical robotic system 700 shown in FIG. 21.

The surgical robotic system 700 has a multi-jointed robotic arm (a transfer means) 702 and a console 704, and the working unit 16 is connected to the distal end of the robotic arm 702. The robotic arm 702 has the same mechanism as the above described actuator block 30, whereby the working unit 16 can be connected thereto and driven. A manipulator 10 in the system has the robotic arm 702 and the working unit 16. The robotic arm 702 may be stationary type, autonomous mobile type, or the like, as long as it can move the working unit 16. The console 704 may be table type (control desk type), control panel type, or the like.

It is preferred that the robotic arm 702 has independent 6 or more joints (rotary shafts, slidable shafts, etc.), because the position and direction of the working unit 16 can be optionally controlled. The distal end 708 of the robotic arm 702 is integral with an actuator block 30.

The actuator block 30 has independent two levers 206 for locking the working unit 16 as described above. The connecting portion 15 has the locking plate 304, which is elastically urged by the coil springs 306 and driven by the alignment pins 212a to 212c. The locking plate 304 can act to lock and unlock the pulleys 50a to 50c.

The robotic arm 702 is driven under the control of the console 704, and may be driven by a program for automatic operation, by a joystick 706 disposed in the console 704, or by a combination thereof. The console 704 has a function of the above-described controller 45.

The console 704 has two joysticks 706 and a monitor 710, and has the same functions as the above described operation command unit 14. The joysticks 706 are used as an operation command unit, provided by removing the actuator block 30 from the operation command unit 14, the operation command unit being controllable in the same manner as the operation command unit 14. Two robotic arms 702 can be independently controlled by the two joysticks 706 though not shown. The two joysticks 706 are positioned such that they can be easily handled by both hands. Information such as an endoscopic image is shown in the monitor 710.

The joysticks 706 can be moved upward, downward, rightward, or leftward, and can be twisted or tilted. The robotic arm 702 is moved in accordance with the motions. Each of the joysticks 706 has a grip handle 26, which has a trigger lever 32, a composite input part 34, and a switch 36. Thus, the joysticks 706 can be handled in the same manner as the operation command unit 14. The joystick 706 may be a master arm. A communication means between the robotic arm 702 and the console 704 may be a wired or wireless means, a network means, or a combination thereof.

While the invention has been particularly shown and described with reference to preferred embodiments, it will be understood that variations and modifications can be effected thereto by those skilled in the art without departing from the spirit and scope of the invention as defined by the appended claims.

What is claimed is:

1. A manipulator for medical use comprising
    an actuator unit containing a motor, and
    a working unit attachable to and detachable from said actuator unit, containing a connecting portion having a rotator connectable to a rotary shaft of said motor and a working portion coupled with said rotator,
    wherein said connecting portion has a locking plate, said locking plate being moved by a part of said actuator unit when said working unit is attached to or detached from said actuator unit,
    said locking plate has an engaging hole, with which a noncircular portion of said rotator is engaged,
    said noncircular portion is engaged with said engaging hole when said working unit is separated from said actuator unit, thereby preventing said rotator from rotating, and said noncircular portion is separated from said engaging hole when said working unit is connected to said actuator unit, thereby making said rotator rotatable.

2. A manipulator for medical use according to claim 1, wherein said actuator unit has a pin extending toward said connecting portion,
    said working unit has an elastic body for pressing said locking plate toward said rotator,
    said locking plate is pressed by said elastic body and said noncircular portion is engaged with said engaging hole when said working unit is separated from said actuator unit, and said locking plate is pushed out by a tip of said pin and said noncircular portion is separated from said engaging hole when said working unit is connected to said actuator unit.

3. A manipulator for medical use according to claim 2, wherein said connecting portion has two or more through-holes, said actuator unit has two or more said pins, and said pins are inserted into said through-holes respectively when said working unit is connected to said actuator unit.

4. A manipulator for medical use according to claim 2, wherein said locking plate has an elongate shape, said working unit has two or more said elastic bodies, and said elastic bodies are positioned distantly in the longitudinal direction of said elongate shape.

5. A manipulator for medical use according to claim 2, wherein said locking plate has an elongate shape and two or more narrow portions, said connecting portion has guide plates at the both sides of each of said narrow portions and a retainer plate connected to an end of each of said guide plates, and said elastic body is placed between said retainer plate and said locking plate.

6. A manipulator for medical use according to claim 1, wherein said noncircular portion has a plate shape, and said engaging hole has a slit shape with a width sufficient for inserting said noncircular portion thereinto.

* * * * *